(12) United States Patent
Tsubaki et al.

(10) Patent No.: US 7,442,541 B2
(45) Date of Patent: Oct. 28, 2008

(54) β-GLUCAN-CONTAINING FAT AND OIL COMPOSITION AND NOVEL MICROORGANISM CAPABLE OF PRODUCING β-GLUCAN

(75) Inventors: Kazufumi Tsubaki, Tokyo (JP); Hiromu Sugiyama, Tokyo (JP); Yoshikazu Shoji, Tokyo (JP)

(73) Assignee: Adeka Corporation, Tokyo (JP)

( * ) Notice: Subject to any disclaimer, the term of this patent is extended or adjusted under 35 U.S.C. 154(b) by 222 days.

(21) Appl. No.: 10/519,379

(22) PCT Filed: Jun. 18, 2003

(86) PCT No.: PCT/JP03/07739

§ 371 (c)(1),
(2), (4) Date: Dec. 27, 2004

(87) PCT Pub. No.: WO04/001053

PCT Pub. Date: Dec. 31, 2003

(65) Prior Publication Data

US 2005/0255126 A1 Nov. 17, 2005

(30) Foreign Application Priority Data

Jun. 25, 2002 (JP) ............................. 2002-185261
Jul. 16, 2002 (JP) ............................. 2002-206994

(51) Int. Cl.
*C12P 1/00* (2006.01)
*C12P 19/00* (2006.01)
*C12N 1/00* (2006.01)
*C12N 1/02* (2006.01)
*A61K 47/00* (2006.01)
*A01N 63/00* (2006.01)

(52) U.S. Cl. ............... 435/254.1; 424/93.5; 424/439; 435/41; 435/72; 435/243; 435/261

(58) Field of Classification Search .................. None
See application file for complete search history.

(56) References Cited

U.S. PATENT DOCUMENTS

| 3,827,937 | A | | 8/1974 | Kato et al. |
| 3,912,591 | A | | 10/1975 | Kato et al. |
| 4,769,363 | A | * | 9/1988 | Misaki et al. ............... 514/54 |
| 4,965,347 | A | | 10/1990 | Misaki et al. |
| 5,019,514 | A | | 5/1991 | Bock et al. |
| 5,480,662 | A | | 1/1996 | Boode-Boissevain et al. |
| 6,426,201 | B1 | | 7/2002 | Morgan |

FOREIGN PATENT DOCUMENTS

| EP | 0 222 302 | 5/1987 |
| EP | 0 236 124 | 9/1987 |
| EP | 0 859 061 | 8/1998 |
| JP | 54-138115 | 10/1979 |
| JP | 62-6692 | 2/1987 |
| JP | 62-111681 | 5/1987 |
| JP | 62-201901 | 9/1987 |
| JP | 3-229702 | 10/1991 |
| JP | 3-272663 | 12/1991 |
| JP | 05-345725 | 12/1993 |
| JP | 6-92441 | 11/1994 |
| JP | 6-340701 | 12/1994 |
| JP | 7-51080 | 2/1995 |
| JP | 09-103266 | 4/1997 |
| JP | 10-167972 | 6/1998 |
| JP | 10-182477 | 7/1998 |
| JP | 11-279204 | 10/1999 |
| JP | 2001-245657 | 9/2001 |
| JP | 2001-247566 | 9/2001 |
| JP | 2001-323001 | 11/2001 |
| JP | 2002-241784 | 8/2002 |
| JP | 2002-306064 | 10/2002 |
| JP | 2003-159011 | 6/2003 |

OTHER PUBLICATIONS

Lachance, et al. Yeast 1997, 13, pp. 225-232.*
Yurlova, N.A., Mokrousov, I.V., de Hoog, G.S. "Intraspecific Variability and Exopolysaccharide Production in Aureobasidium pullulans", Antonie von Leeuwenhoek. 1995, 68, pp. 57-63.*
I. Navarini et al., Structural characterization and solution properties of an acidic branched (1→3)-β-D-glucan from Aureobasidium pullulans, International Journal of Biological Macromolecules Oct. 1996, vol. 19, No. 3, pp. 157 to 163.
K. Sasaki et al., "Further Study of the Structure of Lentinan, an Anti-Tumor Polysaccharide from Lentius Edodes", Carbohydrate Research, vol. 47, 1976, pp. 99-104.
Syokumotusen-I no kagaku, Asakura Shoten, Sep. 5, 1997, p. 108 (English translation of relevant parts) (translation of section 2 only).
Hamada et al., "The Structure of the Carbohydrate Moiety of an Acidic Polysaccharide Produced by Aureobasidium sp. K-1", Agric. Biol. Chem. vol. 47 (6), 1983, pp. 1167-1172.

* cited by examiner

*Primary Examiner*—Cecilia Tsang
*Assistant Examiner*—Aaron J Kosar
(74) *Attorney, Agent, or Firm*—Young & Thompson

(57) ABSTRACT

A β-glucan-containing fat and oil composition contains β-glucan of microorganism origin or basidiomycete origin. The β-glucan-containing fat and oil composition has β-glucan uniformly dispersed in a food without worsening the texture, taste etc. of the food. The novel microorganism can efficiently produce β-glucan which has a high activity and favorable qualities as β-glucan of microorganism origin as described above from less expensive saccharides such as sucrose at a high production speed.

4 Claims, No Drawings

SEQUENCE LISTING

<160> NUMBER OF SEQ ID NOS: 4

<210> SEQ ID NO 1
<211> LENGTH: 1732
<212> TYPE: DNA
<213> ORGANISM: Aureobasidium pullulans ADK-34

<400> SEQUENCE: 1

```
aaagattaag ccatgcatgt ctaagtataa gcaactatac ggtgaaactg cgaatggctc      60
attaaatcag ttatcgttta tttgatagta ccttactact tggataaccg tggtaattct     120
agagctaata catgctaaaa accccaactt cggaaggggt gtatttatta gataaaaaac     180
caacgccctt cggggctcct tggtgattca taataactaa acgaatcgca tggccttgcg     240
ccggcgatgg ttcattcaaa tttctgccct atcaactttc gatggtagga tagtggccta     300
ccatggtatc aacgggtaac ggggaattag ggttctattc cggagaggga gcctgagaaa     360
cggctaccac atccaaggaa ggcagcaggc gcgcaaatta cccaatcccg acacggggag     420
gtagtgacaa taaatactga tacagggctc ttttgggtct tgtaattgga atgagtacaa     480
tttaaatccc ttaacgagga acaattggag ggcaagtctg gtgccagcag ccgcggtaat     540
```

-continued

```
tccagctcca atagcgtata ttaaagttgt tgcagttaaa aagctcgtag ttgaaccttg      600
ggcctggctg gccggtccgc ctcaccgcgt gtactggtcc ggccgggcct ttccttctgg      660
ggagccgcat gcccttcact gggcgtgtcg gggaaccagg actttactt tgaaaaaatt      720 agagtgttca aagcaggcct ttgctcgaat acattagcat ggaataatag aataggacgt      780
gcggttctat tttgttggtt tctaggaccg ccgtaatgat taatagggat agtcgggggc      840
atcagtattc aattgtcaga ggtgaaattc ttggatttat tgaagactaa ctactgcgaa      900
agcatttgcc aaggatgttt tcattaatca gtgaacgaaa gttaggggat cgaagacgat      960
cagataccgt cgtagtctta accataaact atgccgacta gggatcgggc gatgttatca     1020
ttttgactcg ctcggcacct tacgagaaat caaagtcttt gggttctggg gggagtatgg     1080
tcgcaaggct gaaacttaaa gaaattgacg gaagggcacc accaggcgtg gagcctgcgg     1140
cttaatttga ctcaacacgg ggaaactcac caggtccaga cacaataagg attgacagat     1200
tgagagctct ttcttgattt tgtgggtggt ggtgcatggc cgttcttagt tggtggagtg     1260
atttgtctgc ttaattgcga taacgaacga gaccttaacc tgctaaatag cccggcccgc     1320
tttggcgggt cgccggcttc ttagagggac tatcggctca agccgatgga agtttgaggc     1380
aataacaggt ctgtgatgcc cttagatgtt ctgggccgca cgcgcgctac actgacagag     1440
ccaacgagtt catttccttg cccggaaggg ttgggtaatc ttgttaaact ctgtcgtgct     1500
ggggatagag cattgcaatt attgctcttc aacgaggaat gcctagtaag cgtacgtcat     1560
cagcgtgcgt tgattacgtc cctgccctt gtacacaccg cccgtcgcta ctaccgattg     1620
aatggctgag tgaggccttc ggactggccc agggaggtcg caacgacca cccagggccg     1680 gaaagttggt caaactccgt catttagagg aagtaaaagt cgtaacaagg tt               1732
```

```
<210> SEQ ID NO 2
<211> LENGTH: 563
<212> TYPE: DNA
<213> ORGANISM: Aureobasidium pullulans ADK-34

<400> SEQUENCE: 2
```

```
tttccgtagg tgaacctgcg aaggatcat taaagagtaa gggtgctcag cgcccgacct       60 ccaaccttt gttgttaaaa ctaccttgtt gctttggcgg gaccgctcgg ttccgagccg      120
ctggggattc gtcccaggcg agtgcccgcc agagttaaac caaactcttg ttattaaacc      180
ggtcgtctga gttaaaattt tgaataaatc aaaactttca acaacggatc tcttggttct      240
cgcatcgatg aagaacgcag cgaaatgcga taagtaatgt gaattgcaga attcagtgaa      300
tcatcgaatc tttgaacgca cattgcgccc cttggtattc cgaggggcat gcctgttcga      360
gcgtcattac accactcaag ctatgcttgg tattgggtgc cgtccttagt tgggcgcgcc      420
ttaaagacct cggcgaggcc actccggctt taggcgtagt agaatttatt cgaacgtctg      480
tcaaaggaga ggaactctgc cgattgaaac ctttattttt ctaggttgac ctcggatcag      540
gtagggatac cgctgaact taa                                              563
```

```
<210> SEQ ID NO 3
<211> LENGTH: 563
<212> TYPE: DNA
<213> ORGANISM: Aureobasidium pullulans IFO-6353

<400> SEQUENCE: 3
```

```
tttccgtagg tgaacctgcg aaggatcat taaagagtaa gggtgctcag cgcccgacct       60 ccaaccttt gttgttaaaa ctaccttgtt gctttggcgg gaccgctcgg tctcgagccg      120
```

```
ctggggattc gtcccaggcg agcgcccgcc agagttaaac caaactcttg ttatttaacc      180
ggtcgtctga gttaaaattt tgaataaatc aaaactttca acaacggatc tcttggttct      240
cgcatcgatg aagaacgcag cgaaatgcga taagtaatgt gaattgcaga attcagtgaa      300
tcatcgaatc tttgaacgca cattgcgccc cttggtattc cgagggcat gcctgttcga       360 gcgtcattac accactcaag ctatgcttgg tattgggtgc cgtccttagt tgggcgcgcc      420
ttaaagacct cggcgaggcc tcaccggctt taggcgtagt agaatttatt cgaacgtctg      480
tcaaaggaga ggacttctgc cgactgaaac ctttattttt ctaggttgac ctcggatcag      540
gtagggatac ccgctgaact taa                                              563

<210> SEQ ID NO 4
<211> LENGTH: 564
<212> TYPE: DNA
<213> ORGANISM: Aureobasidium pullulans IFO-7757

<400> SEQUENCE: 4
tttccgtagg tgaacctgcg gaaggatcat taaagagtaa gggtgctcag cgcccgacct       60
ccaacccttt gttgttaaaa ctaccttgtt gctttggcgg gaccgctcgg tctcgagccg      120
ctggggattc gtcccaggcg agcgcccgcc agagttaaac caaactcttg ttattaaacc      180
ggtcgtctga gttaaaattt tgaataaatc aaaactttca acaacggatc tcttggttct      240
cgcatcgatg aagaacgcag cgaaatgcga taagtaatgt gaattgcaga attcagtgaa      300
tcatcgaatc tttgaacgca cattgcgccc cttggtattc cgagggcat gcctgttcga       360 gcgtcattac accactcaag ctatgcttgg tattgggtgc cgtccttagt tgggcgcgcc      420
ttaaagacct cggcgaggcc tcaccggctt taggcgtagt agaatttatt cgaacgtctg      480
tcaaaggaga ggacttctgc cgactgaaac cttttatttt tctaggttga cctcggatca      540
ggtagggata cccgctgaac ttaa                                             564
```

β-GLUCAN-CONTAINING FAT AND OIL COMPOSITION AND NOVEL MICROORGANISM CAPABLE OF PRODUCING β-GLUCAN

TECHNICAL FIELD

The present invention relates to a fat and oil composition containing β-glucan originating in microorganisms or basidiomycetes. The fat and oil composition of the invention has β-glucan uniformly dispersed in fat and oil. Added to a food, etc., the composition provides the food with uniformly dispersed β-glucan having bioregulatory functions and also with enhanced taste, texture, and flavor.

The present invention also relates to a novel microorganism useful for obtaining β-glucan and a process of producing β-glucan using the microorganism.

BACKGROUND ART

Beta-glucans are material attracting attention for the utility because of their excellent bioregulatory functions that have recently been analyzed, such as lipid metabolism improving action, intestinal regulatory action, blood sugar controlling action, antitumor effect, and immune enhancing action. Application of such material to a broad range of processed foods will bring extreme benefits, not only contributing to enhancement of functionality of processed foods (addition of value) but matching the expectation of contribution to public health maintenance. Beta-glucans occur in a variety of organisms, including microorganisms, basidiomycetes, and plants, chiefly constituting the skeleton of the organisms. Beta-glucans, for the most part, serve to make up cell walls. Beta-glucans are composed mainly of glucose polymers having at least two kinds of β-1-2,1-3, 1-4, and 1-6-D-glucopyranose bonds.

JP-T-2001-501996 studies β-glucans derived from grains and gramineous plants. Some β-glucans from grains and gramineous plants contain polyphenols, which can cause a coloration problem. Moreover, the β-glucans from these origins are expensive due to low original β-glucan contents, which puts a limit on applicability to foods.

Among microorganisms and basidiomycetes there are strains which secrete the same β-glucan out of fungi as their cell wall component under some cultivation conditions. The cell wall of microorganisms and basidiomycetes contain a large quantity of β-glucan.

Beta-glucan of microorganism or basidiomycete origin, including β-glucan secreted out of fungi by microorganisms or basidiomycetes, β-glucan harvested from microorganisms or basidiomycetes by isolation, extraction, purification or like means, cell wall components of microorganisms or basidiomycetes, and fungi per se, can or could be added to processed foods, for example, as follows. (1) Culture fungi collected from the culture of microorganisms or basidiomycetes are added directly to raw materials of processed foods. (2) Cell wall components of microorganisms or basidiomycetes separated from the culture and purified are added to raw materials of processed foods. (3) Beta-glucan extracted from fungi or separated cell wall components is added to raw materials of processed foods. (4) The supernatant liquid of a culture of microorganisms or basidiomycetes or β-glucan separated and purified from the supernatant liquid is added to raw materials of processed foods.

In view of the fact that many of β-glucans are polymers having a molecular weight of 10,000 or more, and some of them are sparingly soluble in water, it is very difficult to uniformly mix β-glucan with materials of processed foods by the method (1) or (2). Processed foods having β-glucan added thereto by the method (1) or (2) suffer from impairment of texture or reduction of commercial value, such as uneven baking.

The methods (3) and (4) are advantageous in that β-glucan can be incorporated into processed foods relatively uniformly and that the β-glucan content in processed foods can be adjusted freely. However, the extracted and purified β-glucan has problems arising from its high water absorptivity. If such β-glucan is added as such to, for example, a dough mix containing wheat flour as a main ingredient, and the mix is kneaded together with water, the β-glucan forms lumps to make non-uniform dough, which results in processed food products with reduced taste and texture and reduced quality. When β-glucan previously dissolved in water is added to a dough mix (mostly in powder form), the resulting β-glucan-containing foods can have β-glucan dispersed therein relatively uniformly. In this case, however, dissolving β-glucan in water needs much time, the aqueous solution takes on viscosity, and it is not easy to obtain a uniform aqueous solution. Accordingly, to dissolve in water is an impractical operation that impairs the workability on site.

It has therefore been awaited to establish a convenient process for producing processed foods in which β-glucan of microorganism or basidiomycete origin is uniformly dispersed and to develop such a β-glucan material.

Beta-glucans activating the immune system include plant cell wall components (see JP-B-62-6692 and JP-A-2001-323001), those present in the hymenia and the mycelia of basidiomycetes (mushrooms) (see K Sasaki et al., Carbohydrate Res., vol. 47, 99-104 (1976) and JP-A-5-345725), cell wall components of microbial fungi, and those secreted and produced out of fungi.

It is generally well known that the cell wall components of any microorganisms contains β-glucans and exhibit immune enhancement. Among them yeast fungi (see JP-A-54-138115 and JP-A-9-103266), lactic acid bacterial fungi (see JP-A-3-22970 and JP-A-10-167972), fungus of *Aureobasidium* (see JP-B-6-92441), etc. are known to be of high safety and high utility value as foods.

Microorganisms that are known to secrete and produce β-glucan out of fungi exhibiting immune system enhancement include the genus *Macrophomopsis*, the genus *Alcaligenes* producing curdlan (see Syokumotusen-i no kagaku, Asakura Shoten, 1977, 108), and *Aureobasidium pullulans* (see Agaric. Biol. Chem., 47(6), 1983, 1167-1172 and JP-A-6-340701).

The β-glucans present in the hymenia and the mycelia of basidiomycetes (mushrooms) have high immune enhancing activity, and some of them, exemplified by lentinan extracted from the hymenia of *Lentinus edodes*, have been made use of as medicines. In general, however, production of β-glucan by the hymenia and the mycelia of basidiomycetes (mushrooms) greatly varies depending on the growth or cultivation conditions, and it is necessary to separate the β-glucan by extraction. As a result, complicated and wide-ranging molecular species of β-glucan are found in the resulting extract, including both high-molecular-weight ones and low-molecular-weight ones, which means unstable quality.

Thus, stable production of β-glucan with constant high activity is the standing problem relating to basidiomycetes (mushrooms). On the other hand, the cell walls of microorganisms contain a large amount of β-glucan and are of interest as a source of β-glucan. Nevertheless, because the cell walls of microorganisms contain other components than β-glucan and are insoluble in water, they need an extraction operation similarly to basidiomycetes in order to recover highly effective, water-soluble β-glucan. It has therefore been an issue to establish a process for stably extracting β-glucan of constant quality.

In contrast, the fermentation method of producing β-glucan using microorganisms secreting and producing water-soluble β-glucan out of fungi with high immune enhancing activity is an extremely effective technology, making it feasible to obtain uniform, water-soluble, and high-activity β-glucan. Along this line, processes of producing β-glucan using a microorganism belonging to the genus *Aureobasidium* which is known to secrete and produce high-activity β-glucan out of fungi have been proposed.

Microorganisms belonging to the genus *Aureobasidium* are known, however, to secrete and produce pullulan, α-glucan, out of fungi when cultured using carbon sources commonly used in microbial cultivation, such as sucrose (see JP-B-51-36360 and JP-B-51-42199). This has made production of high purity β-glucan difficult (see JP-A-06-340701). Moreover, microorganisms of the genus *Aureobasidium* are also called "black yeast". Black yeast produces melanin pigment, with which the fungi or the culture solution are pigmented in black, and so is the resulting β-glucan. Therefore, the produced β-glucan has seriously ruined product quality. To address this problem, it has been proposed to generate a mutant that does not involve pigmentation by mutagenic treatment and to produce polysaccharides including pullulan by using the mutant (JP-B-4-18835). However, no strain is known that is capable of secreting and producing β-glucan of high purity with good efficiency out of fungi (but incapable of secreting and producing pullulans out of fungi) completely without involving melanin production.

Culturing techniques for the production of β-glucan in which by-production of pullulan, regarded as impurity, during culturing is suppressed have also been studied. JP-A-6-340701 and JP-A-07-51080 propose a process in which pullulan production is controlled by pH adjustment or use of specific sugar as a carbon source thereby to provide β-glucan at high purity. The problem of this process for the production of β-glucan is that the operation is cumbersome because special culturing conditions should be set or that the medium is costly because a special carbon source should be used.

Accordingly, for the production of β-glucan by the use of microorganisms of the genus *Aureobasidium*, a strain is needed that produces no, or a limited amount of, impurity such as pullulan even when cultured using inexpensive saccharides commonly employed in microbial cultivation as a carbon source and that involves substantially no or limited production of pigment melanin during production of β-glucan, thereby secreting and producing high-activity and high-quality β-glucan with good efficiency out of fungi.

DISCLOSURE OF THE INVENTION

An object of the present invention is to provide a β-glucan material that provides a food with uniformly dispersed β-glucan having bioregulatory functions without impairing the taste and texture of the food. Another object of the invention is to provide a novel microorganism that is useful for producing high-activity and high-quality β-glucan from inexpensive saccharides such as sucrose with good efficiency and at high production rates, a process of producing β-glucan using the microorganism, and β-glucan secreted and produced out of fungi by the microorganism.

As a result of extensive investigations, the present inventors have noted use of β-glucan of microorganism or basidiomycete origin and found that dispersing the β-glucan in fats and oils or fat and oil compositions gives β-glucan materials that accomplish the above objects.

Furthermore, for the purpose of accomplishing the above objects, the present inventors have sought for a microorganism capable of secreting and producing high-purity β-glucan out of fungi efficiently. As a result they have found a novel microorganism secreting and producing high-quality β-glucan out of fungi at high efficiency. As a result of further researches, they have reached the finding that a strain belonging to the genus *Aureobasidium* and resistant to the antibiotic cycloheximide is capable of secreting and producing β-glucan out of fungi with high purity at high efficiency.

The present invention provides a β-glucan-containing fat and oil composition characterized by containing β-glucan of microorganism or basidiomycete origin.

The present invention also provides a microorganism of which the 18S rRNA gene contains the sequence of 1732 bases shown in Sequence Listing, SEQ ID No. 1 or a base sequence molecular-phylogenetically equivalent thereto based on the 18S rRNA gene base sequence and which has resistance to the antibiotic cycloheximide and is capable of secreting and producing β-glucan out of fungi.

The present invention also provides a microorganism of which the Internal Transcribed Spacer-5.8S rRNA, or ITS-5.8S rRNA, gene contains the sequence of 563 bases shown in Sequence Listing, SEQ ID No. 2 or a base sequence molecular-phylogenetically equivalent thereto based on the ITS-5.8S rRNA gene base sequence and which is capable of secreting and producing β-glucan out of fungi. It is preferred for this microorganism to have resistance to the antibiotic cycloheximide.

The present invention also provides the above-described microorganisms which are capable of secreting and producing β-glucan having at least a β-1,3-D-glucopyranose bond in the structure out of fungi thereof.

The present invention also provides the above-described microorganisms which belong to the genus *Aureobasidium*.

The present invention also provides the above-described microorganism which is *Aureobasidium pullulans* ADK-34 (FERM BP-8391).

The present invention also provides a process of producing β-glucan comprising culturing any of the above-described microorganisms (preferably in a culture medium containing a saccharide as a carbon source), secreting and producing β-glucan out of fungi.

The present invention also provides a process of producing β-glucan comprising culturing a microorganism of which the ITS-5.8S rRNA gene exhibits sequence homology of at least 98% with the base sequence shown in Sequence Listing, SEQ ID No. 2 (preferably in a culture medium containing a saccharide as a carbon source), secreting and producing β-glucan out of fungi.

The present invention also provides β-glucan which is secreted and produced out of fungi by culturing *Aureobasidium pullulans* ADK-34 (FERM BP-8391) and has at least a β-1,3-D-glucopyranose bond in the structure thereof and a fat and oil composition containing the β-glucan.

The present invention also provides a food containing the above-described β-glucan-containing fat and oil composition according to the present invention and a drug containing the above-described β-glucan-containing fat and oil composition according to the present invention and having preventive activities on habitual diseases (or life-style related diseases).

BEST MODE FOR CARRYING OUT THE INVENTION

The present invention will now be illustrated in detail.

The β-glucan that can be used in the fat and oil composition of the present invention is one originating in a microorganism or a basidiomycete, i.e., one obtained from a microorganism or a basidiomycete.

The β-glucan of microorganism origin useful in the present invention is described first.

Since microbial cells per se contain a large amount of β-glucan in their walls, the "β-glucan of microorganism origin" may be culture cells as obtained by inoculating microorganisms into the respective growth media followed by fungous proliferation or a culture cell wall residue obtained by disrupting the culture cells and removing the cell contents. The "β-glucan of microorganism origin" can also be one extracted from the culture cells or the culture cell wall residue, either as such or as purified. It is also possible to use β-glucan secreted and produced out of fungi by microorganism culturing. In this case, the culture solution after cultivation can be used as such, or β-glucan may be isolated therefrom and purified.

Where the culture cells as obtained by inoculating microorganisms into the respective growth media followed by fungous proliferation are used as they are, the cell contents can reduce the taste or texture or the physical properties of a processed food to which the fat and oil composition is added. It is therefore desirable to use the culture cell wall residue obtained by disrupting the culture cells and removing the cell contents. It is more desirable to use the β-glucan extracted from the culture cells or the culture cell wall residue either as such or as purified. It is the most desirable to use the secreted and produced β-glucan out of fungi either together with the culture solution or after isolated and purified.

Microorganisms suitable for obtaining β-glucan are those that have hitherto been used in food industries and proved highly safe. Such microorganisms include yeasts, lactic acid bacteria, natto bacteria, acetic acid bacteria, koji bacteria, algae, such as *Chlorella* and *Spirulina*, and microorganisms belonging to the genus *Aureobasidium*. These microorganisms can be those isolated from the environment (such as a food, soil or a room). Stock strains or isolated strains or mutants obtained from stock strains or isolated strains by ordinary mutation operations can be used. Useful mutation operations include UV irradiation and treatments with chemicals such as nitrosoguanidine, ethidium bromide, methane ethyl sulfonate, and sodium nitrite.

The yeasts include those classified into the genus *Saccharomyces* that are used in making alcohols (such as beer, carbonated alcohols, shochu (Japanese distilled liquor), sake, wine, and whisky) or bread; compressed yeast; those used in making soy sauce; and those of the genus *Candida* used in the production of single-cell protein.

The lactic acid bacteria that are usually used include bacilli, such as those of genera *Lactobacillus* and *Bifidobacterium*, and cocci, such as those of genera *Leuconostock, Pediococcus, Streptococcus*, and *Lactococcus*. In addition, lactic acid bacteria of the genera *Enterococcus, Vagococcus, Carnobacterium, Aerococcus*, and *Tetragenococcus* are also useful. More specifically, one or more of the following traditionally utilized lactic acid bacteria species can be used: *Lactobacillus bulgaricus, L. helveticus, L. acidophilus, L. lactis, L. casei, L. brevis, L. plantarum, L. sake, Streptococcus thermophilus, S. lactis, S. cremoris, Bifidobacterium longum, B. bifidum, B. breve, B. infantis, Leuconostoc cremoris, Ln. mesenteroides, Ln. ocnos, Pediococcus acidilactici, P. cerevisiae*, and *P. pentosaceus*. These species can be used either individually or as a combination of two or more thereof. A lactic acid bacterium of the genus *Bifidobacterium* and another lactic acid bacteria may be cultured separately, and the cultures may be mixed.

The microorganisms belonging to the genus *Aureobasidium* are not limited as long as they are capable of producing glucose polymers having a β-bond out of fungi when cultured. Strains of *Aureobasidium pullulans*, e.g., IFO 4467, IFO 4466, IFO 6353, IFO 7757, ATCC 9348, ATCC 3092, ATCC 42023, and ATCC 433023, are mentioned as examples. The microorganisms isolated from the environment (e.g., foods, soil, rooms) can be used. Stock strains or isolated strains or mutants obtained from stock strains or isolated strains by ordinary mutation operations can also be used. Useful mutation operations include UV irradiation and treatments with chemicals such as nitrosoguanidine, ethidium bromide, methane ethyl sulfonate, and sodium nitrite.

Additional microorganisms that can be used include natto bacteria of the genus *Bacillus*, acetic acid bacteria of the genus *Acetobactor*, koji bacteria of the genus *Aspergillus*, bacteria of the genus *Penicillium*, algae, e.g., *Chlorella* and *Spirulina*, dry *chlorella* powder, strains of the genus *Aureobasidium* known capable of secreting and producing pullulan out of fungi, and strains of the genera *Xanthomonas, Aeromonas, Azotobactor, Alcaligenes, Erwinia, Enterobactor, Sclerotium, Pseudomonas, Agrobacterium*, and *Macrophomopsis* known capable of producing thickening polysaccharides useful as food additives.

The microorganisms that are suited for use in the present invention include the novel ones according to the invention, i.e., a microorganism of which the 18S rRNA gene contains the sequence of 1732 bases shown in Sequence Listing, SEQ ID No. 1 or a base sequence molecular-phylogenetically equivalent thereto based on the 18S rRNA gene base sequence and which is resistant to the antibiotic cycloheximide and capable of secreting and producing β-glucan out of fungi and a microorganism of which the ITS-5.8S rRNA gene contains the sequence of 563 bases shown in Sequence Listing, SEQ ID No. 2 or a base sequence molecular-phylogenetically equivalent thereto based on the ITS-5.8S rRNA gene base sequence and which is capable of secreting and producing β-glucan out of fungi. The novel microorganisms of the invention will be described later in greater detail.

The β-glucan of basidiomycete origin that can be used in the present invention is then described hereunder.

Since basidiomycetes contain a large amount of β-glucan in the hymenium and the sclerotium, a compact mass of hyphae, either of finely ground hymenium or sclerotium and an extract from the ground hymenium or sclerotium, either as such or as purified, can be used as β-glucan of basidiomycete origin. Culture cells obtained by germinating spores of basidiomycetes, inoculating the mycelia into the respective culture media, followed by fungous proliferation can also be used as such. A culture cell wall residue prepared by disrupting the culture cells and removing the cell contents can also be used. Beta-glucan extracted from the culture cells or the culture cell wall residue can also be used as β-glucan of basidiomycete origin, either as such or after purification. It is also possible to use β-glucan secreted and produced out of fungi by culturing basidiomycetes. In this case, the culture solution after cultivation can be used as such or after isolation and purification of the β-glucan.

Where the finely ground hymenium or sclerotium or the β-glucan extracted therefrom or the culture cells as obtained by inoculating spores or mycelium into the respective growth media followed by fungous proliferation are used as they are, the cell contents can reduce the taste or texture or the physical properties of a processed food to which the fat and oil composition is added. It is therefore desirable to use the culture cell wall residue obtained by disrupting the culture cells and removing the cell contents. It is more desirable to use the β-glucan extracted from the culture cells or the culture cell wall residue either as such or as purified. It is the most desirable to use the secreted and produced β-glucan out of fungi either together with the culture solution or after separated from the culture solution and purified.

While the most preferred basidiomycetes for use in the invention are cultivated varieties, β-glucan from basidiomycetes that are not in commercial production are useful as well. Useful species include *Agaricus blazei, Morchella esculenta* (common morel), *Suillus bovinus, Climacodon septentrionalis, Flammulina velutipes, Fistulina hepatica, Auricularia auricula, Dictyophora indusiata, Naematoloma sublateritium, Stropharia rugosoannulata, Coprinus comatus, Hericium ramosum, Lentinus edodes, Rhizopogon rubescens, Tremella fuciformis, Lyophyllum ulmayium, Pleurocybella porrigens, Pleurotus cornucopiae, Polyporus umbellatus, Pleurotus dryinus, Cordyceps, Pholiota nameko, Armillariella mellea, Armillariella tabescens, Tricholoma giganteum, Gloeostereum incarnatum, Pseudohydnum gelatinosum, Pholiota adiposa, Pholiota aurivella, Lactarius hatsudake, Pleurotus ostreatus, Wolfiporia cocos, Volvariella volvacea, Hypsizigus marmoreus, Myceleptodonoides aitchisonii, Lyophyllum shimeji, Grifola frondosa, Laetiporus sulphureus, Lentinus lepideus, Agaricus bisporus, Tricholoma matsutake, Ganoderma lucidum, Panellus serotinus, Lepista nuda, Boletus edulis, Hericium erinaceum*, and *Agrocybe cylindracea*.

A culture cell wall residue as β-glucan of the above-recited microorganisms and basidiomycetes can be obtained by, for example, a method comprising adding an adequate amount of a solvent to cultured microorganisms, cultured mycelia, cultured sclerotia or cultured hymenia, destroying part of the cell walls by autodigestion or by addition of a hydrolase to allow the contents to flow out, and collecting the residue as β-glucan or a method comprising applying a physical force by a French press, an ultrasonic processor, etc. to the cells to destroy part of the cells, removing the cell contents, and collecting the residue as β-glucan.

Beta-glucan can be extracted by any method. Extraction is effected by adding an extracting solvent to the extraction material, the microorganism or basidiomycete. Usable extracting solvents include water, salt solutions, aqueous acid solutions, aqueous alkali solutions, organic solvents, and mixtures of two or more thereof. A combined use of a cell wall degrading enzyme will increase the extraction efficiency. The extract may be used in any form and at any purity. That is, the extract separated by solid-liquid separation of the extraction system may be used as such, or the extract may be concentrated in a usual manner to liquid or solid, or the extract may be purified in a known manner into liquid or solid with increased purity. It does not matter if the extract contains any extracted component other than β-glucan. In the present invention all these product forms are called β-glucan extracted from microorganisms or basidiomycetes.

The method of extracting β-glucan from microorganisms or basidiomycetes will be described further. The β-glucan used in the invention is a water-soluble polymer dissolving in a solvent such as water. For example, a commercially available mushrooms, i.e., a basidiomycete is dried and ground to powder, and the powder is extracted with 2 to 100 times the amount of water, warm water, hot water, a salt solution, an aqueous acid or alkali solution, an organic solvent, etc. at an arbitrary temperature for an arbitrary period of time. The extraction system is separated into liquid and solid to recover the extracted β-glucan. Beta-glucan extracted with water, warm water or hot water is preferred. Beta-glucan extracted with water at temperature of 4° to 80° C. is still preferred. An extraction accelerator, such as an enzyme solution, may be added to the system.

The β-glucan used in the invention is preferably one having at least two kinds of a β-1-2-D-glucopyranose bond, a β-1-3-D-glucopyranose bond, a β-1-4-D-glucopyranose bond, and a β-1-6-D-glucopyranose bond. Beta-glucan having a β-1,3-D-glucopyranose bond and a β-1,4-D-glucopyranose bond, one having a β-1,3-D-glucopyranose bond and a β-1,6-D-glucopyranose bond, and one having a β-1-3-D-glucopyranose bond, a β-1-4-D-glucopyranose bond, and a β-1-6-D-glucopyranose bond are particularly preferred. It should be noted that so-called curdlan composed of β-1,3-D-glucopyranose bonds is not included under the β-glucan of the invention.

The β-glucan used in the invention is a high-molecular-weight compound. While β-glucan having any weight average molecular weight is usable, one having a molecular weight of less than 3,000,000, preferably less than 500,000, still preferably less than 100,000 is suitable because the compatibility with fats and oils increases as the molecular weight decreases. The molecular weight of extracted β-glucan may be reduced in a conventional manner to have improved compatibility with fats and oils, or low-molecular β-glucan may be directly obtained by extraction.

The fats and oils or fat and oil compositions in which the β-glucan of microorganism or basidiomycete origin or originating in the novel microorganisms according to the invention is dispersed are not particularly limited as long as they are edible. Examples are rice oil, rapeseed oil, soybean oil, cotton seed oil, palm oil, palm kernel oil, coconut oil, olive oil, fish oil, beef tallow, lard, cacao butter; processed oils derived from these fats and oils according to necessity, such as hydrogenated oils, slightly hydrogenated oils, hydrogenation isomerized oils, interesterified oils, and fractionated oils; fats and oils processed by two or more of the recited processes; and mixtures of two or more of these fats and oils. Additionally, disperse systems using these edible fats and oils as a dispersing medium or a dispersoid, such as emulsions (including W/O emulsions, O/W emulsions, double emulsions, i.e., O/W/O emulsions and W/O/W emulsions, and more complex multiple emulsions) and suspensions, are also useful (such disperse systems will hereinafter be included under the category "fats and oils").

The β-glucan-containing fat and oil composition of the present invention is obtained by adding the β-glucan to the above-recited fat and oil, followed by mixing.

When added to fats and oils, the form of the β-glucan is not particularly limited and can be added as such or as dissolved in water or any other water-soluble solvents.

Where the fat and oil is an emulsion, the β-glucan may be dispersed in a previously prepared fat and oil emulsion or be dispersed at the time of emulsification. While it is possible to add the β-glucan to either the oily phase or the aqueous phase, it is preferred that the β-glucan be first dispersed in the oily phase and then mixed with the aqueous phase. By so doing, the β-glucan will exhibit satisfactory compatibility with fat and oil to give a homogeneous β-glucan-containing fat and oil composition in a shorter time.

Where the fat and oil is a water-in-oil emulsion, a plasticized water-in-oil emulsion, etc., addition of the β-glucan may be followed by emulsification, or be simultaneous with emulsification, or be preceded by emulsification as stated above, or be preceded by plasticization. In using solid fat, it may be softened or liquefied by an appropriate method according to necessity before mixing the β-glucan. In order to highly uniformly disperse the β-glucan, it is desirable that 100 parts by weight of powdered β-glucan and 10 to 50 parts by weight of fat and oil are mixed, and the mixture is then subjected to rolling or a combination of rolling and conching. Other raw materials, an additional amount of oil or fat, and the like may be added in this stage to adjust the β-glucan content in the final β-glucan-containing fat and oil composition.

While the manner of the mixing following the addition of the β-glucan to the fat and oil is not particularly restricted, it is advisable to maintain the mixture of the β-glucan and the fat and oil at 50° C. or higher for a given period of time, preferably 5 minutes to 6 hours, still preferably 10 minutes to 2 hours, thereby to obtain a β-glucan-containing fat and oil composition in which the β-glucan is uniformly dispersed with sufficient compatibility with the fat and oil. Foods prepared using the thus prepared β-glucan-containing fat and oil composition have the β-glucan dispersed therein more uniformly than those prepared by directly adding β-glucan to foodstuffs. As a result, there are observed remarkable effects such that the taste or texture is not impaired, suppression of flavor due to use of an emulsifier is unexpectedly reduced, and the flavor of foodstuffs is brought out more.

The means for mixing β-glucan into fats and oils include various types of machines for mixing, kneading or stirring. Examples are propeller agitators, oscillatory mixers, orifice mixers, paddle agitators, agitation emulsifiers (homomixer), cutter mixers, cokneaders, conches, silent cutters, jet mixers, vacuum agitators, screw mixers, static mixers, cutting mixers, ultrasonic emulsifiers, kneaders, rolls, Hydrossure, pipeline mixers, universal mixers, pin machines, homogenizers (high-pressure homogenizers), ball cutters, and ribbon mixers. It is preferred to use an agitation emulsifier (homomixer) and/or a homogenizer (high-pressure homogenizer) at a product temperature of 40° to 80° C.

After mixing the β-glucan and the fat and oil by agitation, the resulting β-glucan-containing fat and oil composition may be stored as obtained, or emulsified, or rapidly cooled for plasticization. For plasticization, a votator, a combinator, a perfector, a complector, Onreitor, etc. can be used. Use of a pin machine at a product temperature of 10° C. or lower is preferred. It is also possible that the fat and oil is previously emulsified and processed in a rapid cooling-plasticizing apparatus, such as a votator, a combinator, a perfector, a complector or Onreitor, and the β-glucan is then added, followed by mixing by any of the above-described methods to prepare a βglucan-containing fat and oil composition.

The β-glucan content in the fat and oil composition of the present invention is preferably 0.01 to 500 parts by weight, still preferably 0.1 to 150 parts by weight, particularly preferably 1 to 100 parts by weight, per 100 parts by weight of the total of the components other than the β-glucan. Where the β-glucan content is less than 0.01 parts by weight, a final product tends to fail to exhibit the functional effects of β-glucan. If it exceeds 500 parts by weight, the mixture tends to become powdery or lumpy irrespective of the kinds of other ingredients, failing to provide an edible fat and oil composition having a β-glucan mixed and dispersed therein uniformly. Even after the mixture is processed into a final product, it is very likely that the lumps would remain only to cause non-uniform distribution of the β-glucan.

Where an extract from a microorganism or a basidiomycete is used as such without being purified or merely after being powdered or solidified, an acceptable purity of the β-glucan in the extract ranges 1 to 100%. A preferred purity is from 10 to 100%, particularly 20 to 100%. The higher the better.

It is possible to add, to the β-glucan-containing fat and oil composition of the present invention, food additives such as emulsifiers, gelling agents, thickeners, and stabilizers so as to ensure preventing the β-glucan from getting distributed non-uniformly due to agglomeration into lumps in the composition. The food additives are not particularly limited as far as they are edible. Examples of the emulsifiers are lecithin, fatty acid monoglycerides, sorbitan fatty acid esters, propylene glycol fatty acid esters, and sugar esters. Examples of the thickeners and the stabilizers are pullulan, psyllium, gum arabic, gellan gum, glucomannan, guar gum, xanthan gum, tamarind gum, carrageenan, alginic acid salts, farceran, locust bean gum, pectin, curdlan, and low-molecular compounds derived from these substances; starch, processed starch, gelatinized starch, crystalline cellulose, gelatin, dextrin, agar, and dextran. Additional useful food additives include saccharides, such as glucose, fructose, sucrose, maltose, enzyme-saccharified sugar (thick malt syrup), lactose, reducing starch saccharification products, isomerized liquid sugar, sucrose-coupled malt syrup, oligosaccharides, reducing sugar polydextrose, sorbitol, reduced lactose, trehalose, xylose, xylitol, maltitol, erythritol, mannitol, fructo-oligosaccharides, soybean oligosaccharides, galacto-oligosaccharides, lactosucrose-oligosaccharides, raffinose, lactulose, palatinose-oligosaccharides, stevia, and Aspartame; stabilizers, such as phosphoric acid salts (e.g., hexametaphosphates, secondary phosphates and primary phosphates), and alkali metal (e.g., potassium or sodium) salts of citric acid; proteins, such as whey proteins, (e.g., α-lactalbumin, β-lactoglobulin, and serum albumin), casein and other milk proteins, low-density lipoprotein, high-density lipoprotein, egg proteins (e.g., phosvitin, livetin, phosphoglycoprotein, ovalbumin, conalbumin, and ovomucoid), wheat proteins (e.g., gliadin, glutenin, prolamine, and glutelin), and other vegetable and animal proteins; inorganic salts, such as sodium chloride, rock salt, sea salt, and potassium chloride; souring agents, such as acetic acid, lactic acid, and gluconic acid; colorants, such as β-carotin, caramel, and Monascus color; antioxidants, such as tocopherol and tea extract; eggs, such as whole eggs, egg yolk, egg white, and enzyme-processed eggs; cereals, such as bread flour, all-purpose flour, and cake flour; beans, such as soybean powder; water, flavors, dairy products, seasonings, pH adjustors, enzymes, food preservatives, shelf life extenders, fruits, fruit juices, coffee, nut pastes, spices, cacao mass, and cocoa powder. Two or more of these additives can be used in combination. The amounts of the additives to be added are not particularly limited. They can be added in general amounts, for example, 0.01 to 15% by weight based on the composition.

The foods according to the present invention will now be described hereunder. The foods of the invention contain the aforementioned β-glucan-containing fat and oil composition as a part or the whole of the fat and oil ingredients conventionally employed therein. Included in such foods are not only fat and oil foods exemplified by margarine and shortening but any kinds containing fats or oils, such as bakery products, confectionery products, processed rice products, processed wheat products, processed maize products, processed soybean products, health foods, and medicinal foods. The β-glucan-containing fat and oil composition of the present invention substitutes for a part of, or the whole of, fats and oils in these foods to provide foods that can be served in a conventional manner irrespective of whether the foods are liquid (e.g., salad oil, frying oil, and whipping cream), sol (e.g., liquid shortening), paste or emulsion (e.g., foamable emulsified fats, dressings, fat spreads, custard cream, and dipping cream) or solid (e.g., shortening, margarine, candies, chocolates, and roux type curry sauce mixes).

The bakery products of the present invention are described below. The bakery products contain the aforementioned β-glucan-containing fat and oil composition. The bakery products are produced by baking dough prepared by substituting a part or the whole of fats and oils conventionally employed in making bakery products by the β-glucan-containing fat and oil composition. The bakery products include breads, pies, kasutera (Japanese style sponge cake), sponge cakes, butter cakes, puff pastries, waffles, and fermented confections. The method of preparing dough is not particularly limited, except that a part of or the whole of the fat and oil which have been conventionally used in dough preparation is substituted with the β-glucan-containing fat and oil composition of the present invention. In making bread as an example of the bakery products, bread dough is prepared from common raw materials of bread, such as wheat flour, water, yeast, sugar, and edible salt, and the β-glucan-containing fat and oil composition of the invention by a known dough preparation method. For instance, after mixing the other materials, the β-glucan-containing fat and oil composition is folded into the mix. The resulting dough is then fermented, shaped, and baked in a usual manner. Similarly, the β-glucan-containing fat and oil composition of the invention can be used as a substitute for a part of or the whole of fat and oil for folding (roll-in fat and oil) or fat and oil for dough and batter in making folded pies; a part of or the whole of pieces of fat and oil in the form of chips, straws, etc. in making pie crusts; or a part of or the whole of foamable emulsified fat and oil or liquid oil for cakes in making sponge cakes.

Where the production of bakery products involves a baking step, if a microorganism or a basidiomycete is added as such as a β-glucan source or even when β-glucan is directly added to dough or a powder mix, which is then kneaded into dough, lumps are easily formed in the dough. Dough containing such lumps only provides a bakery product with a rough or grainy texture or a strange texture due to non-uniform moisture distribution or non-uniform firmness. To the contrary, use of the β-glucan-containing fat and oil composition of the invention provides dough having the β-glucan uniformly dispersed therein with very few lumps, which finally gives a baked product with a good texture, not only free from a strange texture but with greatly improved softness.

The confectionery products are then described. The confectionery products contain the aforementioned β-glucan-containing fat and oil composition of the invention. The confectionery products are produced by processing dough prepared by substituting a part or the whole of fats and oils conventionally employed in making confectionery products with the β-glucan-containing fat and oil composition. The confectionery products include deep-fried products such as snacks and doughnuts and steamed products such as steamed cakes and bean-jam buns. Another type of the confectionery products includes candies, gums, chocolates, and tablets prepared by mixing the β-glucan-containing oil and fat composition with sugar, flavors, and the like and, if necessary, solidifying and molding the mixture. Cold desserts, such as sherbet, are also included under confectionery products.

In making confectionery products, where the weight is put on not only flavor but taste, particularly sweetness, it is more important to eliminate lumps. Even a very small lump would cause a strange feeling and ruin the commercial value. Since the β-glucan-containing fat and oil composition according to the present invention previously contains β-glucan in a uniformly dispersed state, even when it is added to and mixed with a premixed material, there is provided a final confectionery product containing the β-glucan in a uniformly dispersed state with no lumps and having a good flavor with no strange taste.

The β-glucan-containing fat and oil composition according to the present invention can be added to foods or drugs containing a food ingredient having a prophylactic action for habitual diseases to enhance the action of the foods or drugs. Such foods or drugs include those containing unsaturated higher fatty acids regulating a blood lipid concentration (e.g., EPA and DHA), plant sterols regulating blood serum cholesterol and esters thereof; diacylglycerol, γ-linolenic acid, α-linolenic acid, beet fiber, corn (maize) fiber, psyllium seed coat, tea polyphenol, lecithin; dried bonito peptide, sardine peptide, casein dodecapeptide, and soybean protein isolate which are effective in lowering blood pressure; and lactic acid bacteria, gluconic acid, oligosaccharides, and various dietary fibers which improve the intestinal environment to regulate the intestines. Furthermore, foods or drugs with enhanced bioregulatory functions can be obtained by adding the β-glucan-containing fat and oil composition of the present invention to substances known to have health improving functionality, such as *Chlorella, Spirulina*, propolis, chitin, chitosan, nucleic acids, leyss (*Ganoderma lucidum*), agaricus, ginkgo leaf extract, lakanka (Lo Hon Go), turmeric, garcinia, apple fiber, gymnema, collagen, blueberry, aloe, saw palmetto, plant fermentation enzymes, soybean isoflavon, chlorophyll, royal jelly, Asian ginseng, prune, and herbs, such as chamomile, thyme, sage, peppermint, lemon balm, mallow, oregano, cat nip tea, yarrow, and hibiscus.

When added to processed foods of rice, wheat, maize or soybeans, the β-glucan-containing fat and oil composition of the present invention is capable of imparting functionality to these foodstuffs or enhancing the functionality of the foodstuffs. Examples of such processed foods are boiled rice products (e.g., frozen boiled rice and sterile boiled rice); processed rice products, such as rice noodles, rice chips, and rice crackers; the above-recited bakery products and confectionery products; noodles, such as pastas, buckwheat noodles, udon noodles, houtou noodles, and Chinese noodles; other wheat processed foods; breakfast cereals or processed maize products such as corn flakes; and processed soybean products, such as tofu, soybean milk, soybean milk beverages, yuba (soybean milk skin), thin fried tofu, thick fried tofu, round fried tofu, soybean jam, and miso (soybean paste). Additionally, the fat and oil composition can be added to a variety of foods, including dairy products, such as milk, processed milk, yogurt, whey beverages, fermented lactic acid beverages, butter, and cheese; Japanese sweets, such as yokan (bean jelly), monaka (wafer with bean jam), and sweet bean jam; soups, such as potage, stew, and curry; seasonings, such as soy sauce, Worcester sauce, dips, jams, and tomato ketchup; processed meat products, such as sausage; and processed marine products, such as steamed fish paste, baked fish paste and fried fish paste.

Among the known microorganisms suited for obtaining β-glucan are those of the genus *Aureobasidium*. The present invention provides novel microorganisms advantageous for the production of β-glucan. The following is the details of the novel microorganisms.

The microorganisms provided in the present invention are a microorganism of which the 18S rRNA gene contains the sequence of 1732 bases shown in Sequence Listing, SEQ ID No. 1 or a base sequence molecular-phylogenetically equivalent thereto based on the 18S rRNA gene base sequence and which is resistant to the antibiotic cycloheximide produced by *Streptomyces griseus*, etc. and capable of secreting and producing β-glucan out of fungi and a microorganism of which the ITS-5.8S rRNA gene contains the sequence of 563 bases shown in Sequence Listing, SEQ ID No. 2 or a base sequence molecular-phylogenetically equivalent thereto based on the ITS-5.8S rRNA gene base sequence and which is capable of secreting and producing β-glucan. The microorganism preferably has resistance to the antibiotic cycloheximide produced by *Streptomyces griseus*, etc.

As long as the above-mentioned characteristics are possessed, any strains can be used, including wild strains, stock strains, strains deposited with culture collections, mutants (induced by UV irradiation or treatment with chemicals, e.g., N-methyl-N'-nitrosoguanidine (NTG), acridine, ethane methane sulfonate (EMS), and nitrous acid), and improved strains obtained through biological/genetic engineering technology involving cell fusion, genetic modification, and the like.

The microorganisms of the present invention are obtained from the environment, for example, foods, vegetables, fruits, indoor and outdoor air (on settling plates), floors, walls, ceilings, roofs, mortar, concrete, tile joints, shower curtains, plastic cloth, refrigerators, washing machines, bathtubs, indoor dust, plant body surfaces, soil, river water, lake water, and sea water.

The present inventors have separated the microorganisms of the invention from the environment as demonstrated in Examples given infra. Among the separated microorganisms of the invention are found those belonging to the genus *Aureobasidium*. In particular, a strain capable of secreting and producing non-colored, high-purity β-glucan out of fungi with good efficiency was designated ADK-34. This strain was deposited with International Patent Organism Depositary, the National Institute of Advanced Industrial Science and Technology (address: Tsukuba Central 6, 1-1-1 Higashi, Tsukuba, Ibaraki, Japan; post code: 305-8566) on Jun. 2, 2003 as labeled "*Aureobasidium pullulans* ADK-34" (labeling for identification of microorganism), given accession number FERM BP-8391.

Drug resistance of a strain, namely the drug concentration at which a strain shows resistance can vary depending on the conditions of the strain, the kind of the medium, and the cultivation time. The expression "resistant to cycloheximide" as used herein shall mean "exhibiting resistance to cycloheximide compared with reference strains, IFO-4466, IFO-6353, and IFO-7757". This is the case that the formation of a colony of 0.1 mm or greater, preferably 0.3 mm or greater, still preferably 0.5 mm or greater in diameter as a result of fungous proliferation is observed on a solid medium having the cycloheximide concentration that IFO strains is not allowed to grow after a strain is inoculated on the solid medium (agar plate) containing cycloheximide and cultured at 26° C. for 10 days. Usually, these IFO strains are not allowed to grow on a solid medium containing cycloheximide at concentrations of 20 µg/ml or higher.

Whether a strain, a culture or β-glucan is "non-colored" or "with suppressed coloration" as used herein is evaluated as follows. A culture is diluted appropriately and centrifuged (10000×g, 10 mins) to remove the fungi. The absorbance of the resulting diluted culture solution at 490 nm is measured. The strain, culture or β-glucan under test is called "non-colored" or "with suppressed coloration" when the absorbance thus measured is 0.099 or lower, preferably 0.060 or lower, still preferably 0.050 or lower, under conditions such that a diluted culture solution of IFO-6353 strain prepared in the same manner has an absorbance of 0.1 or higher at 490 nm.

The term "high purity" as used in the invention is intended to have the following meaning. In the measurement of purity with respect to the produced polysaccharide pullulan as demonstrated in Analysis Example 3 described infra, a phenol-sulfuric acid value of a test system is measured before and after treatment with pullulanase (enzyme). When the ratio of the value after the enzyme treatment to that before the enzyme treatment is 75% or higher, the purity of the produced β-glucan is said to be high. That ratio is preferably 85% or higher, still preferably 90% or higher.

The term "fungi" as used in the he invention is intended to include not only molds, yeasts and mushrooms, but also microorganisms (inclusive of bacteria) themselves and their cells irrespective of whether they are dead or alive.

The microorganisms of the present invention are suitable for extracellular production of β-glucan with high purity at high efficiency. The β-glucan produced by the microorganisms of the invention is preferably one having at least a β-1,3-D-glucopyranose bond in its structure.

The process of producing β-glucan using the microorganisms of the invention will be described with reference to its preferred embodiments.

According to the process, production of β-glucan using the microorganisms of the invention is achieved by causing a strain of the microorganism of the invention to act on a medium allowing the strain to grow to produce β-glucan out of fungi in the medium. The production of β-glucan out of fungi can also be achieved by separating culture fungi obtained by culturing a strain of the microorganism of the invention and causing the culture fungi to act on a solution or medium containing saccharides that are a substrate of β-glucan. There are cases wherein secretive β-glucan that is ready to be secreted out of fungi is present within the fungi. In the present invention, such β-glucan accumulated in the fungi and ready to be secreted is also included under the term "secreted β-glucan out of fungi".

The media in which a strain of the microorganisms of the invention is cultured in the process of producing β-glucan using the microorganisms of the invention include ordinary ones containing nutrients (including carbon sources, nitrogen sources, and inorganic salts) microorganisms belonging to the genus *Aureobasidium* can usually utilize. The media may further contain organic nutrients if needed. Liquid media containing saccharides as a carbon source are preferred. Any of various synthetic media, semisynthetic media, natural media, and the like is usable.

The carbon sources preferably include saccharides. The saccharides include monosaccharides, such as glucose, fructose, mannose, galactose, xylose, and arabinose; disaccharides, such as sucrose, maltose, lactose, and treharose; oligosaccharides, such as fructo-oligosaccharides and xylo-oligosaccharides; and polysaccharides, such as dextrin and starch. The saccharides can be used either individually or as a combination thereof. It is still preferred to use, among them, hexoses, such as glucose and fructose; disaccharides, such as sucrose and lactose; or polysaccharides, such as starch, dextrin, and hydrolyzates of such carbohydrates. Beet juice, sugarcane juice, fruit juices such as citrus juice, or mixtures of these juices, either as such or sweetened, are also useful. Additionally, other carbon sources including alcohols, such as glycerol and ethylene glycol, sugar alcohols, such as mannitol, sorbitol, and erythritol, and organic acids are also used appropriately. These carbon sources may be added during cultivation as needed. For example, it is preferred that a saccharide such as sucrose be appropriately fed to the medium to keep its concentration within a range of from 3 to 500 g/l, still preferably 5 to 300 g/l, particularly preferably 10 to 200 g/l, thereby to relatively increase the rate and amount of production of β-glucan.

The nitrogen sources include organic ones, such as peptone, meat extract, soybean flour, casein, amino acids, malt extract, corn steep liquor, casein decomposition products, yeast extract, and urea; and inorganic ones, such as sodium nitrate, ammonium sulfate, ammonia gas, and aqueous ammonia; and mixtures thereof.

The inorganic salts include sodium chloride, potassium chloride, calcium carbonate, magnesium sulfate, sodium phosphate, potassium phosphate, cobalt chloride, and heavy metal salts. If desired vitamins may be used. Where foaming occurs during cultivation, known defoamers may be added to the medium appropriately.

The cultivation conditions for the microorganism strains of the invention are not particularly limited and can be chosen from the ranges allowing the strains to grow satisfactorily. Generally recommended conditions are pH of 5.0 to 8.5, 20° to 35° C., and about 2 to 8 days. These cultivation conditions are subject to variation according to the kind and characteristics of the strain, external conditions, and so forth and can be selected to give the best results. The amount of strains to be inoculated into a medium is preferably one platinum loopful for flask cultivation. For increased scale production, a seed culture is added to a main culture in an amount of 1 to 10% (v/v) based on the main culture. These amounts are not limitative as long as cultivation is possible.

The microorganism strains of the invention are cultivated under aerobic conditions with aeration-agitation, shaking, and the like. Cultivation is conducted until a desired β-glucan concentration is reached, usually for 2 to 5 days. Beta-glucan production may be conducted in a continuous manner by continuously feeding a saccharide, a β-glucan's substrate, or other medium components. The saccharide such as sucrose as a β-glucan's substrate can be added in the form of powder or syrup (thick solution in water) in an amount of 0.1 to 500 g per liter of the culture solution. Addition of more than 500 g/l results in great reduction of production speed. After addition of the substrate, the culture reaction is allowed to proceed preferably at 25° to 35° C. for 1 to 7 days, desirably about 2 to 5 days, under aerobic conditions with shaking, aeration-agitation or like operation to produce β-glucan from the saccharide substrate, such as sucrose.

It is possible to use culture fungi obtained by cultivating the microorganism strain of the invention or an extract of the culture fungi as a catalyst for producing β-glucan. In this case, a solution or medium containing a saccharide as a substrate is added to a suspension of the culture fungi, a suspension of the prepared culture fungi or a suspension of the treated culture fungi. The prepared culture fungi include a disrupted cell solution prepared by homogenizing the culture fungi. The treated culture fungi include immobilized fungi obtained by immobilizing the culture fungi or the disrupted cell solution with alginate gel, ion-exchange resins, ceramics, chitosan, etc. Solutions that can be used to prepare the suspension of the culture fungi, the prepared or treated culture fungi include the above-described media and one of, or a mixture of one or more of, buffer solutions of tris-acetic acid, tris-hydrochloric acid, sodium succinate, sodium citrate, sodium phosphate, potassium phosphate, etc. The pH of the buffer solutions is preferably 3.5 to 9.0, still preferably 5.0 to 8.0, particularly preferably 5.2 to 7.8. The culture fungi concentration in the suspension is, while not limitative, suitably about 0.1% to 10% on a wet volume basis.

The solution or medium containing saccharides as a substrate can be added to the suspension in any amount at any concentration, but it is preferred that the amount of the substrate added each time be within a range that maintains the activity of the fungi. For example, 0.1 to 500 g of the substrate may be added all at once or in several divided portions, or the substrate may be added continuously at a rate of about 0.5 to 500 g/day, both per liter of the suspension. The solution containing the fungi and the substrate is incubated at a given temperature for a given period of time to produce β-glucan. The incubation is preferably carried out under the same conditions as for the cultivation of the aforementioned microorganism strains of the invention.

After the cultivation, the secreted and produced β-glucan out of fungi is separated and harvested from the culture in a usual manner. Specifically, the solid matter, fungi etc., is separated and removed from the culture by centrifugation, filtration or like means, and the separated culture solution may be purified by an appropriate combination of known methods for removing impurities and salts, such as treatment with activated carbon, ion-exchange resins, etc. The thus harvested β-glucan may further be purified by any one of, or an appropriate combination of, or a repetition of, additional purification methods including adsorption-desorption using hydrophobic resins, solvent precipitation using ethanol, methanol, ethyl acetate, n-butanol, etc., column or thin film chromatography using silica gel, etc., and preparative high performance liquid chromatography using reverse phase columns.

The fungi may be sterilized either before or after separating the secreted and produced β-glucan out of fungi by the above-described methods. The sterilization temperature is not particularly limited as long as the fungi are killed but preferably 500 or higher, still preferably 60° C. or higher, particularly preferably 80° C. or higher. The temperature may be further raised, e.g., to 90° C. or higher, or at 121° C. under pressure, whereby the secretive β-glucan accumulated within the fungi and ready to be secreted out of fungi can be extracted with hot water. While the sterilization time or the hot water extraction time is arbitrarily selected, a period of from 10 minutes to 8 hours, preferably 15 minutes to 6 hours, particularly preferably 30 minutes to 2 hours is suitable for controlling incorporation of impurity and preventing deterioration of the β-glucan.

Beta-glucan can also be produced in the same manner as described above, except for replacing the microorganism according to the present invention with a microorganism of which the ITS-5.8S rRNA gene exhibits sequence homology of at least 98% with the base sequence shown in Sequence Listing, SEQ ID No. 2.

It is preferred to use *Aureobasidium pullulans* ADK-34 (FERM BP-8391) for the production of β-glucan because the resulting β-glucan has at least a β-1,3-D-glucopyranose bond in the structure thereof.

The β-glucan production process using the microorganisms according to the invention is advantageous over the processes using known strains of *Aureobasidium pullulans* or other microorganisms belonging to the genus *Aureobasidium* in that the production of *pullulan* is significantly suppressed. That is, the produced β-glucan can be isolated from the culture more easily, and the purification operation for recovering high purity β-glucan can be simplified. Besides, the β-glucan produced by using the microorganisms of the invention is less impure and remarkably less colored than β-glucan extracted from the fungous cell walls of other microorganisms of the genus *Aureobasidium*, yeasts, lactic acid bacteria, etc. or from basidiomycetes or plants. Therefore, the produced β-glucan can be isolated and purified through simplified operations to give high and constant quality β-glucan in a stable manner with ease.

Being free from coloration and of high quality, the β-glucan obtained in the present invention can be used in a wide variety of applications as they are or as incorporated into other products.

Applications of the β-glucan obtained in the present invention include foods, food additives, cosmetics, toiletries, chemical products, drugs, and so forth.

Specific examples of the foods are listed below.

Processed fat and oil foods include margarine, shortening, mayonnaise, cream, salad oil, frying oil, whipping cream, foamable emulsified fats, dressings, fat spreads, custard cream, and dipping cream. Because the β-glucan obtained in the present invention has excellent compatibility with fats and oils as previously stated, it is preferred that the β-glucan be added to fats and oils to give fat and oil compositions containing the β-glucan (i.e., the β-glucan-containing fat and oil compositions according to the present invention), which are used together with other raw materials.

Grain-related products include foods made mainly from wheat flour, foods made mainly from rice, processed rice products, processed wheat products, processed corn products, and processed soybean products. Examples are bakery products, such as bread, dessert bread, and Danish pies; pancakes, doughnuts, pizza, tempura, and premixes thereof; cookies/biscuits and snacks; noodles, such as raw noodles, dry noodles, packaged instant noodles, instant cup noodles, udon noodles, buckwheat noodles, Chinese noodles, rice noodles, and pastas; and rice products, such as boiled rice, rice cake, sterile boiled rice, retort pouch boiled rice, nonglutinous rice flour, glutinous rice flour, dumplings, rice crackers, and rice chips.

Confectionery products include Japanese or European ones, such as chocolates, candies, drops, chewing gums, baked confections, cakes, and sweet bean-jam buns.

Processed meat products include ham, sausage, and hamburgers. Processed marine products include baked fish paste, steamed fish paste, fried fish paste, and fish sausage.

Dairy products include butter, cheese, ice cream, and yogurt.

Beverages include alcoholic beverages, e.g., beer, sake, whisky, brandy, shochu, distilled liquors, sparkling alcohols, wines, and fruit wines; coffee, tea, green tea, woolong tea, Chinese tea, cocoa, carbonated beverages, nutritious drinks, sports drinks, coffee drinks, lactic acid beverages, fruit juices, and fruit drinks.

Seasonings and sauces include spices, dips, dressings for meat, salad dressings, Worcester sauce, miso, soy sauce, and roux type sauce mixes, e.g., curry sauce mixes and hashed beef sauce mixes. Soups include corn soup, potato soup, and pumpkin soup. Jams, peanut butter, and toppings are also included in foods.

The foods also include preserved foods, such as canned or bottled foods of fishes and shells, meats, fruits, vegetables, mushrooms, corned beef, jams, tomatoes, etc.; frozen foods; retort pouch foods, such as curry, stew, meat sauce, ma-po tofu, stew of meat with vegetables, soups, and boiled rice; and powdered foods, such as instant powder foods, e.g., powdered beverages, powdered soups, and powdered miso soup.

The foods also include special health foods, medicated foods, nursery foods, such as baby foods, invalid diets (e.g., liquid diets), diets for the old, fat-reducing diets, and supplementary foods.

Microwave foods ready to be reheated or cooked are also included in foods.

The food additives include emulsifiers, thickeners, thickening stabilizers, food quality improvers, antioxidants, stabilizers, preservatives, flavors, sweeteners, colorants, bleaches, souring agents, gum bases, seasonings, bittering agents, nutrient enhancers, spices, and other non-categorized food additives.

The cosmetics and toiletries include skin care cosmetics, hair care cosmetics, medicated cosmetics, and oral care products. Examples include basic skin care cosmetics, such as skin lotions, milky lotions, skin milks, creams, ointments, lotions, calamine lotions, sun screens, suntan products, aftershave lotions, pre-shave lotions, makeup bases, beauty masks, facial cleansers, facial washes, antiacne cosmetics, and essences; makeup cosmetics, such as foundations, face powders, eye shadows, eye liners, eyebrow colors, cheek colors, lipsticks, and nail colors; shampoos, hair rinses, hair conditioners, hair dyes, hair tonics, waveset lotions, hair dressings, hair growth tonics, pilatories, body powders, deodorants, depilatories, soaps, body shampoos, hand cleaners, perfumes, tooth pastes, oral care preparations, and bathing preparations.

The chemical products include surface active agents, emulsifiers, thickeners, and viscosity modifiers.

The drugs include those having cholesterol reducing effect, intestinal regulatory effect, blood sugar controlling effect, and the like and therefore effective in preventing habitual diseases, and drugs having immune enhancing action.

The present invention will now be illustrated in greater detail with respect to Examples, but it should be understood that the invention is not construed as being limited thereto. Unless otherwise noted, all the parts and percents are by weight.

ANALYSIS EXAMPLE 1

Confirmation of β-Glucan and Determination of β-Glucan Content

Analysis of β-glucan in polysaccharides was carried out by first determining the total polysaccharide content that settled out of an alcohol solution by the phenol-sulfuric acid method and then confirming and determining β-glucan in the precipitated polysaccharides. The conformation and determination of β-glucan were performed with an assay kit for detecting β-glucan having a β-1,3-D-glucopyranose bond, available from Seikagaku Corp. The analytical procedures are described below.

The total polysaccharide content in a sample was measured by the phenol-sulfuric acid method as follows. To 30 μl of a sample solution was added 30 μl of distilled water, and 120 μL of a phosphate buffer solution containing 300 mM NaCl (pH 6.9) was added thereto. To the mixture was added 540 μl (three times the volume) of ethanol, and the system was allowed to stand at −15° C. for 10 minutes to precipitate polysaccharides. The supernatant liquid was removed, and 100 μl of distilled water was added to the residue to dissolve it. To the solution were added 100 μl of a 5 wt % aqueous phenol solution and 500 μl of sulfuric acid and allowed to react. The absorbance of the reaction solution at 490 nm was measured. A blank was prepared by adding 100 μl of a 5 wt % aqueous phenol solution and 500 μl of sulfuric acid to 100 μl of distilled water containing no sample, and the absorbance of the blank at 490 nm was also measured. A two-fold dilution series was prepared from 10 mg/ml pullulan as standard samples. A calibration curve was prepared using the standard samples, and the total polysaccharide content in the sample under analysis was obtained from the calibration curve and the absorbances.

A sample solution having a total polysaccharide content of about 0.1 to 1 mg/ml was 10-fold diluted with 1.0M NaOH and the $10^{10}$-fold diluted with β-glucan-free distilled water. Into a test tube was put 50 µl of the resulting β-glucan dilution, and 50 µl of the main reaction reagent of the kit was added, followed by incubation at 37° C. for 30 minutes. Subsequently, 50 µl of a prepared sodium nitrite solution, 50 µl of ammonium sulfamate, and 50 µl of a prepared N-methyl-2-pyrrolidone solution were added to cause reaction. The absorbance of the reaction solution at 545 nm (reference wavelength: 630 nm) was measured. Beta-glucan solutions having concentrations of from 7.5 to 60 pg/ml were prepared using the attached β-glucan standard reagent to prepare a calibration curve. The concentration of the β-glucan dilution was calculated from the calibration curve and the absorbance thereby to obtain the β-glucan content in the sample under analysis.

ANALYSIS EXAMPLE 2

Measurement of Molecular Weight of β-Glucan

The molecular weight of β-glucan was measured as follows. A sample was mixed with three times as much alcohol, cooled to −20° C., and allowed to stand for 10 minutes to obtain a precipitate. A 5 mg portion of the precipitated β-glucan was put into a test tube, and 1 ml of distilled water was added thereto. The precipitate was dissolved in a boiling water bath. The solution was filtered through a 0.22 µm filter to prepare a sample for HPLC. The sample was analyzed by HPLC using a gel-filtration column, Shodex-packed column KS-805 (available from Showa Denko K. K.) at a flow rate of 0.6 ml/min at a temperature of 50° C. An RI detector was used for detection, water was used as a developing solvent, and Shodex Pullulan Standard P-82 (Showa Denko K. K.) was used as a molecular weight marker.

ANALYSIS EXAMPLE 3

Measurement of Purity wrt Polysaccharide Pullulan in Culture

The purity with respect to polysaccharide pullulan produced in the culture was determined using pullulanase (available from Wako Pure Chemical Industries, Ltd.), an enzyme specifically decomposing pullulan. That is, the amount of the polysaccharides was measured before and after the enzymatic digestion with pullulanase, and the purity with respect to the produced polysaccharide pullulan was calculated from the amount of the polysaccharides after the enzymatic treatment (i.e., the amount of the polysaccharides that had not been-digested with pullulanase) and the total amount of the polysaccharides before the enzymatic treatment. The details of the polysaccharide determination are described below.

A mixture of 50 µl of a diluted pullulanase solution and 2 ml of a citrate buffer solution (containing 10 mmol/l citric acid and 20 mmol/l phosphate buffer; pH 6.0) was used as an enzyme solution. A diluted solution (10 mg/ml) of pullulan (available from Tokyo Kasei Kogyo Co., Ltd.) was used as a standard sample solution positive control). Two 30 µl portions of each of a culture solution under analysis and the standard sample were put into the respective 1.5-ml volume test tubes. Into one of the tubes was added 30 µl of the enzyme solution, and 30 µl of PBS into the other, followed by allowing the systems to react at 37° C. for 1 hour. After the reaction, three times as much ethanol as the contents was added to each tube, and the contents were stirred well and incubated at −15° C. for 10 minutes, followed by centrifugal separation at 4° C. and 15000 rpm for 10 minutes. The supernatant liquid was discarded, and the residue was dried. To the resultant solid was added 100 µl of distilled water, the mixture stirred, and 100 µl of a 5 wt % aqueous phenol solution added, and 500 µl of sulfuric acid added immediately, to cause color reaction. After cooling, the reaction solution was dispensed in 100 µl portions into a 96-well microplate. The absorbance at 490 nm was measured. A mixture of distilled water, a 5 wt % aqueous phenol solution, and sulfuric acid was used as a blank. A calibration curve was prepared using pullulan solutions diluted from 10 mg/ml to 1 µg/ml concentrations. The polysaccharide contents in the culture solution before and after the enzymatic digestion were obtained from the calibration curve and the absorbances, from which the purity with respect to the polysaccharide pullulan in the culture solution was calculated. When the standard sample (pullulan solution) was enzymatically digested, the digestion rate achieved was 90% or higher at a concentration of 10 mg/ml, 95% or higher at 1 mg/ml, and 98% or higher at 0.1 mg/ml or lower concentrations. Thus, where pullulan had been produced, the phenol-sulfuric acid value (absorbance) decreased after the treatment with the enzyme pullulanase. In case when, for example, the absorbance decreased by 50%, the purity with respect to the polysaccharide pullulan was calculated to be 50%.

PREPARATION EXAMPLE 1

Preparation of β-Glucan of Mushroom Origin

1) Preparation of Mushroom Extract

The hymenia of *Agaricus blazei* were ground. To 10 kg of the ground material was added 50 liters of hot water. The suspension was gently stirred while boiling for 3 hours to conduct hot water extraction, followed by centrifugal separation to obtain an extract.

2) Purification of Mushroom Extract

To the extract obtained in (1) above was added three times as much 99% ethyl alcohol. The thus formed precipitate was collected and lyophilized to give 1200 g of a crude product (crude β-glucan of mushroom origin, designated sample A). The β-glucan content per gram of sample A was calculated to 860 mg. The molecular weight at the peak was 1,000,000.

3) Preparation of Enzymatically Treated Mushroom Extract

One kilogram of the hymenia of *Agaricus blazei* was ground in a mixer with 2 liters of water. Two grams of Funcelase (from Yakult Pharmaceutical Ind. Co., Ltd.) was added thereto and mixed, followed by incubation at 55° C. for 3 hours for enzymatic reaction. The reaction system was heated to 85° C. and maintained at that temperature for 10 minutes to deactivate the enzyme. Three liters of distilled water was added, and the mixture was stirred well. The solid matter was removed to give 4.5 liters of an extract (enzymatically treated β-glucan extract of mushroom origin, designated sample B). The β-glucan content per milliliter of sample B was calculated to be 93 mg. The molecular weights were distributed between 10,000 and 800,000, with the peak molecular weight being 120,000.

4) Preparation of Mushroom Mycelium Culture

Into each of four 500 ml volume Erlenmeyer flasks was put 120 ml of a glucose-potato extract medium (glucose 2%; potato 200 g/l) and sterilized at 120° C. for 30 minutes. The hyphae of *Flammulina velutipes* IFO-30602 separately maintained on a slant culture medium were inoculated into the medium and cultured in a rotary incubator at 25° C. and 200 rpm for 10 days. The cultures from the four flasks were combined, washed with physiological saline, and lyophilized to obtain 8 g of dry mycelia. One gram of the resulting mycelia was extracted with 10 ml of a 0.2M aqueous sodium hydroxide solution at 15° C. for one day with stirring. The extraction system as such was adjusted to pH 3.0 with hydrochloric acid, autoclaved at 120° C. for 30 minutes, and centrifuged. The separated supernatant liquid was adjusted to pH 7.0 with disodium phosphate, and three times as much ethyl alcohol was added. The thus formed precipitate was collected, and 10 ml of distilled water was added thereto to obtain sample C. The β-glucan content in sample C was calculated to be 40 mg per milliliter. The molecular weight at the peak was 200,000.

PREPARATION EXAMPLE 2

Preparation of β-Glucan of Microorganism Origin

1) Preparation of Microbial Cell Wall

Fungi were suspended at a concentration of 1 g/ml in water having 0.5% lysolecithin dissolved therein. The suspension was treated on an ultrasonic disrupter for 10 minutes, followed by centrifugal separation to remove the supernatant liquid. The solid was lyophilized to obtain a cell wall component. The cell wall obtained from a commercially available powdered lactic acid bacterium (from Morinaga Milk Industry Co., Ltd.) was designated sample D. The cell wall obtained from commercially available compressed yeast (Dia Yeast from Kyowa Hakko Kogyo Co., Ltd.) was designated sample E. The cell wall obtained from commercially available dry *chlorella* (*Chlorella* Micropowder from *Chlorella* Kogyo Co., Ltd.) was designated sample F. Ten milligrams of each sample was extracted with 1 ml of 1M sodium hydroxide aqueous solution at 50° C. for one day. The supernatant liquid (extract) separated by centrifugation was diluted with distilled water to prepare a 10-fold to 100-fold dilution series to carry out β-glucan content determination. As a result, the β-glucan content per 10 mg of Samples D, E, and F was found to be 2.8 mg, 4.9 mg, and 3.5 mg, respectively. The molecular weight was then measured. Ten milligrams of each sample was extracted with 1 ml of 1M sodium hydroxide aqueous solution at 50° C. for one day, followed by centrifugation. To the separated supernatant liquid was added three times as much ethanol. The precipitate thus formed was dissolved in 1 ml of distilled water. Samples D, E, and F were found to have a weight average molecular weight of 1,200,000, 2,000,000, and 1,800,000, respectively.

PREPARATION EXAMPLE 3

Preparation of Alkali Extract From Cell Walls

1) Preparation of Alkali Extract From Fungal Cell Walls

A hundred grams of *Sparassis crispa* was extracted with 1 liter of 1% sodium hydroxide at 65° C. for 2 hours with stirring. The extraction residue was removed by centrifugation. The extract was neutralized with HCl, and an equivalent amount of ethanol was added thereto to recover 20 g of a precipitate (β-glucan extracted with fungal cell walls, designated sample G). The β-glucan content per gram of sample G was calculated to be 500 mg. The peak molecular weight was 1,200,000.

2) Preparation of Alkali Extract From Microbial Cell Walls

A hundred grams of cell walls prepared from commercially available compressed yeast (sample E) was extracted with 1 liter of 2% sodium hydroxide at 4° C. for 24 hours. The extract solution separated by centrifugation was neutralized with HCl, and double the amount of ethanol was added thereto to collect 20 g of a solid extract (β-glucan extracted from yeast cell walls, designated sample H). The β-glucan content per 10 grams of sample H was calculated to be 4.2 mg. The peak molecular weight was 1,600,000.

PREPARATION EXAMPLE 4

Preparation of Microbial Culture

1) Preparation of Lactic Acid Bacterium Culture

A culture medium was prepared by mixing, in ratio, 5 g of polypepton, 5 g of yeast extract, 5 g of glucose, 1 g of $MgSO_4 \cdot 7H_2O$, and 1 liter of distilled water and adjusting to pH 5.5. *Pediococcus damnosus* (IFO-3896 at Institute for Fermentation, Osaka) was inoculated into 5 liters of the medium and cultured at 30° C. for 5 days with agitation (50 rpm) and without aeration in duplicate. The combined culture (10 liters) was centrifuged, and the separated supernatant liquid was concentrated to 2 liters under reduced pressure. To the concentrate was added double the volume of ethanol, and the formed precipitate was collected and lyophilized to give 15 g of a lactic acid culture as powder (designated sample I). The β-glucan content per gram of sample I was calculated to be 600 mg. The peak molecular weight was 1,900,000.

2) Preparation of *Aureobasidium* Culture

*Aureobasidium pullulans* IFO-7757, which is a genetically and morphologically identified microorganism belonging to the genus *Aureobasidium* and capable of producing a glucose polymer having a β-bond out of fungi, cultured on a potato-dextrose-agar slant was used as a stock strain. The strain was inoculated into 100 ml of YM liquid medium (from Difco) in a 500 ml volume Erlenmeyer flask and pre-cultured at 28° C. for 3 days. The resulting preculture was put into a 5 liter volume fermentation tank equipped with impellers "FULLZONE" containing 3 liters of Czapek's medium (from Difco) and cultured at 28° C. for 5 days. 1 During the culturing, the medium was adjusted at pH 5.0, and the aeration rate was set at 1 vvm by sequentially controlling the amount of air and the number of revolution. The culture (3 liters) was sterilized by heating at 90° C. for 30 minutes and centrifuged to remove the fungi. One liter of the culture solution was lyophilized to give 27 g of a freeze-dried *Aureobasidium* culture, designated sample J. The β-glucan content per gram of sample J was calculated to be 440 mg. To a 10 mg/ml solution of sample J in distilled water was added a suspension of enzyme pullulanase (from Wako Pure Chemical) to give an enzyme concentration of 0.05%. After allowing the system to react for 2 hours, double the quantity of ethanol was added thereto. The thus precipitated solid was re-dissolved in 1 ml of distilled water to measure the molecular weight. For control, a 10 mg/ml solution of pullulan in distilled water was treated in the same manner to measure the molecular weight. Sample J had a peak molecular weight of 200,000, whereas the pullulan solution showed no molecular peak.

To the rest of the culture (2 liters) was added double the volume of ethanol, and the formed precipitate was collected and freeze-dried to give 26 g of a purified *Aureobasidium* culture as powder, designated sample K. The β-glucan content per 10 milligrams of sample K was calculated to be 6 mg. To a 10 mg/ml solution of sample K in distilled water was added a suspension of enzyme pullulanase (from Wako Pure Chemical) to give an enzyme concentration of 0.05%. After allowing the system to react for 2 hours, double the quantity of ethanol was added thereto. The thus precipitated solid was re-dissolved in 1 ml of distilled water to measure the molecular weight. For control, a 10 mg/ml solution of pullulan in distilled water was treated in the same manner to measure the molecular weight. Sample K had a peak molecular weight of 200,000, whereas the pullulan solution showed no molecular peak.

EXAMPLE 1

Beta-Glucan-Containing Fat and Oil Composition

A hundred parts of sample A and 100 parts of soybean oil were thoroughly mixed in a kneader. The mixture was allowed to stand at 60° C. for 10 minutes and then cooled to room temperature, whereupon it became creamy to give a β-glucan-containing fat and oil composition-i according to the present invention (β-glucan content: 43%). The β-glucan was found uniformly dispersed in the composition.

EXAMPLE 2

Beta-Glucan-Containing Fat and Oil Composition

Eighty parts of sample B and 120 parts of soybean oil were thoroughly mixed in a kneader. The mixture was allowed to stand at 60° C. for 10 minutes and then cooled to room temperature, whereupon it became creamy to give a β-glucan-containing fat and oil composition-2 according to the present invention (β-glucan content: 3.7%). The β-glucan was found uniformly dispersed in the composition.

EXAMPLE 3

Beta-Glucan-Containing Fat and Oil Composition

A hundred parts of sample H and 100 parts of soybean oil were thoroughly mixed in a kneader. The mixture was allowed to stand at 60° C. for 10 minutes and then cooled to room temperature, whereupon it became creamy to give a β-glucan-containing fat and oil composition-3 according to the present invention (β-glucan content: 21%). The β-glucan was found uniformly dispersed in the composition.

EXAMPLE 4

Beta-Glucan-Containing Fat and Oil Composition

To three hundred parts of sample K were added 100 parts of palm oil having been melted at 70° C. and 1 part of lecithin, followed by mixing in a high-speed homomixer. The mixture was left to stand at 50° C. for 20 minutes and then cooled to room temperature to give a lumpy β-glucan-containing fat and oil composition-4 according to the present invention (β-glucan content: 44.9%). The β-glucan was found uniformly dispersed in the composition.

EXAMPLE 5

Beta-Glucan-Containing Fat and Oil Composition

To three hundred parts of sample E were added 100 parts of palm oil having been melted at 70° C. and 1 part of lecithin, followed by mixing in a high-speed homomixer. The mixture was left to stand at 50° C. for 20 minutes and then cooled to room temperature to give a lumpy β-glucan-containing fat and oil composition-5 according to the present invention (β-glucan content: 36.6%). The β-glucan was found uniformly dispersed.

EXAMPLE 6

Beta-Glucan-Containing Fat and Oil Composition

To three hundred parts of sample F were added 100 parts of palm oil having been melted at 70° C. and 1 part of lecithin, followed by mixing in a high-speed homomixer. The mixture was left to stand at 50° C. for 20 minutes and then cooled to room temperature to give a lumpy β-glucan-containing fat and oil composition-6 according to the present invention (β-glucan content: 26%). The β-glucan was found uniformly dispersed.

EXAMPLE 7

Beta-Glucan-Containing Fat and Oil Composition

To fifty parts of sample G were added 30 parts of palm olein oil, 70 parts of rapeseed oil, and 0.2 parts of protease-hydrolyzed egg yolk, followed by mixing in a mixer. The mixture was left to stand at 65° C. for 15 minutes and then cooled to room temperature to give a creamy β-glucan-containing fat and oil composition-7 according to the present invention (β-glucan content: 16.6%). The β-glucan was found uniformly dispersed.

EXAMPLE 8

Beta-Glucan-Containing Fat and Oil Composition

To fifty parts of sample I were added 30 parts of palm olein oil, 70 parts of rapeseed oil, and 0.2 parts of protease-hydrolyzed egg yolk, followed by mixing in a mixer. The mixture was allowed to stand at 65° C. for 15 minutes and then cooled to room temperature to give a creamy β-glucan-containing fat and oil composition-8 according to the present invention (β-glucan content: 20%). The β-glucan was found uniformly dispersed in the composition.

EXAMPLE 9

Beta-Glucan-Containing Fat and Oil Composition

To fifty parts of sample K were added 30 parts of palm olein oil, 70 parts of rapeseed oil, and 0.2 parts of protease-hydrolyzed egg yolk, followed by mixing in a mixer. The mixture was allowed to stand at 65° C. for 15 minutes and then cooled to room temperature to give a creamy β-glucan-containing fat and oil composition-9 according to the present invention (β-glucan content: 20%). The β-glucan was found uniformly dispersed.

EXAMPLE 10

Beta-Glucan-Containing Fat and Oil Composition

To five parts of sample A were added 40 parts of rice oil, 20 parts of olive oil, and 35 parts of safflower oil, followed by mixing in a high-speed homomixer. The resulting mixture was allowed to stand at 50° C. for 30 minutes and then cooled to room temperature to give a β-glucan-containing fat and oil composition-10 according to the present invention (β-glucan content: 4.3%), which had almost the same viscosity as the raw material oils but showed slight turbidity. The β-glucan was found uniformly dispersed in the composition.

EXAMPLE 11

Beta-Glucan-Containing Fat and Oil Composition

To five parts of sample I were added 40 parts of rice oil, 20 parts of olive oil, and 35 parts of safflower oil, followed by mixing in a high-speed homomixer. The resulting mixture was allowed to stand at 50° C. for 30 minutes and then cooled to room temperature to give a β-glucan-containing fat and oil composition-11 according to the present invention (β-glucan content: 3%), which had almost the same viscosity as the raw material oils but showed slight turbidity. The β-glucan was found uniformly dispersed.

EXAMPLE 12

Beta-Glucan-Containing Fat and Oil Composition

To five parts of sample J were added 40 parts of rice oil, 20 parts of olive oil, and 35 parts of safflower oil, followed by mixing in a high-speed homomixer. The resulting mixture was allowed to stand at 50° C. for 30 minutes and then cooled to room temperature to give a β-glucan-containing fat and oil composition-12 according to the present invention (β-glucan content: 2.2%), which had almost the same viscosity as the raw material oils but showed slight turbidity. The β-glucan was found uniformly dispersed.

EXAMPLE 13

Beta-Glucan-Containing Fat and Oil Composition

To thirteen parts of sample G were added 20 parts of hardened soybean oil (melting point: 45° C.), 35 parts of palm oil, 30 parts of cotton seed oil, and 0.2 parts of soybean lysolecithin. After being allowed to stand at 70° C. for 10 minutes, the mixture was emulsified in a high-speed mixer and rapidly cooled for plasticization to give a β-glucan-containing fat and oil composition-13 according to the present invention having margarine-like physical properties (β-glucan content: 6.6%). The β-glucan was found uniformly dispersed in the composition.

EXAMPLE 14

Beta-Glucan-Containing Fat and Oil Composition

To thirteen parts of sample H were added 20 parts of hardened soybean oil (melting point: 45° C.), 35 parts of palm oil, 30 parts of cotton seed oil, and 0.2 parts of soybean lysolecithin. After being allowed to stand at 70° C. for 10 minutes, the mixture was emulsified in a high-speed mixer and rapidly cooled for plasticization to give a β-glucan-containing fat and oil composition-14 according to the present invention having margarine-like physical properties (β-glucan content: 5.6%). The β-glucan was found uniformly dispersed.

EXAMPLE 15

Beta-Glucan-Containing Fat and Oil Composition

To thirteen parts of sample K were added 20 parts of hardened soybean oil (melting point: 45° C.), 35 parts of palm oil, 30 parts of cotton seed oil, and 0.2 parts of soybean lysolecithin. After being allowed to stand at 70° C. for 10 minutes, the mixture was emulsified in a high-speed mixer and rapidly cooled for plasticization to give a β-glucan-containing fat and oil composition-15 according to the present invention having margarine-like physical properties (β-glucan content: 8%). The β-glucan was found uniformly dispersed.

EXAMPLE 16

Beta-Glucan-Containing Fat and Oil Composition

To fifty parts of sample B were added 27.6 parts of hardened fish oil (melting point: 36° C.), 18 parts of corn salad oil, and 0.4 parts of glycerol monotartrate. The mixture was stirred at 50° C. for 30 minutes, emulsified in a high-speed mixer, and rapidly cooled for plasticization to give a β-glucan-containing fat and oil composition-16 according to the present invention having fat spread-like physical properties (β-glucan content: 4.8%). The β-glucan was found uniformly dispersed.

EXAMPLE 17

Beta-Glucan-Containing Fat and Oil Composition

To fifty parts of sample H were added 27.6 parts of hardened fish oil (melting point: 36° C.), 18 parts of corn salad oil, and 0.4 parts of glycerol monotartrate. The mixture was stirred at 50° C. for 30 minutes, emulsified in a high-speed mixer, and rapidly cooled for plasticization to give a β-glucan-containing fat and oil composition-17 according to the present invention having fat spread-like physical properties (β-glucan content: 22%). The β-glucan was found uniformly dispersed.

EXAMPLE 18

Beta-Glucan-Containing Fat and Oil Composition

To fifty parts of sample I were added 27.6 parts of hardened fish oil (melting point: 36° C.), 18 parts of corn salad oil, and 0.4 parts of glycerol monotartrate. The mixture was stirred at 50° C. for 30 minutes, emulsified in a high-speed mixer, and rapidly cooled for plasticization to give a β-glucan-containing fat and oil composition-18 according to the present invention having fat spread-like physical properties (β-glucan content: 31%). The β-glucan was found uniformly dispersed.

EXAMPLE 19

Beta-Glucan-Containing Fat and Oil Composition

To twenty parts of sample G were added 0.3 parts of olive oil (melting point: 36° C.) and 0.1 parts of sodium casein. The mixture was left to stand at 55° C. for 15 minutes, emulsified in a high-speed mixer, and spray-dried to give a β-glucan-containing fat and oil composition-19 according to the present invention in powder form (β-glucan content: 49%). The β-glucan was found uniformly dispersed.

EXAMPLE 20

Beta-Glucan-Containing Fat and Oil Composition

To twenty parts of sample H were added 0.3 parts of olive oil (melting point: 36° C.) and 0.1 parts of sodium casein. The mixture was allowed to stand at 55° C. for 15 minutes, emulsified in a high-speed mixer, and spray-dried to give a β-glucan-containing fat and oil composition-20 according to the present invention in powder form (β-glucan content: 41%). The β-glucan was found uniformly dispersed.

EXAMPLE 21

Beta-Glucan-Containing Fat and Oil Composition

To twenty parts of sample K were added 0.3 parts of olive oil (melting point: 36° C.) and 0.1 parts of sodium casein. The mixture was allowed to stand at 55° C. for 15 minutes, emulsified in a high-speed mixer, and spray-dried to give a β-glucan-containing fat and oil composition-21 according to the present invention in powder form (β-glucan content: 59%). The β-glucan was found uniformly dispersed.

EXAMPLE 22

Production of Shortening

An oil phase consisting of 30 parts of palm oil, 50 parts of hydrogenated palm oil, 20 parts of rapeseed oil, and 0.3 parts of lecithin was melted at 70° C. To 100 parts of the oil phase was added 5.0 parts of sample G, and the mixture was allowed to stand at 70° C. for 30 minutes. The mixture was agitated in a homomixer at a high rotational speed for 2 minutes to prepare a β-glucan-containing fat and oil composition-22 according to the present invention. The β-glucan was found by visual observation sufficiently dispersed in the fat and oil phase. The composition was rapidly cooled for plasticization and cooled to 5° C. to obtain shortening (β-glucan content: 2.4%) according to the present invention. The resulting shortening was evaluated for smoothness and flavor. The results obtained are shown in Table 1. It is understood that the resulting shortening is superior to that of Comparative Example 1 described later in smoothness and flavor. Although the step of crystal aging had been omitted, the shortening can be said to enjoy the effects of forming moderate crystals with excellent texture, accelerating such crystallization, and minimizing reduction of flavor by the emulsifier.

EXAMPLE 23

Production of Shortening

An oil phase consisting of 30 parts of palm oil, 50 parts of hydrogenated palm oil, 20 parts of rapeseed oil, and 0.3 parts of lecithin was melted at 70° C. To 100 parts of the oil phase was added 5.0 parts of sample K, and the mixture was allowed to stand at 70° C. for 30 minutes. The mixture was then agitated in a homomixer at a high rotational speed for 2 minutes to give a β-glucan-containing fat and oil composition-23 according to the present invention. The β-glucan was found by visual observation thoroughly dispersed in the fat and oil. The composition was rapidly cooled for plasticization and cooled to 5° C. to obtain shortening (β-glucan content: 2.9%) according to the present invention. The resulting shortening was evaluated for smoothness and flavor. The results obtained are shown in Table 1. It is seen that the resulting shortening is superior to that of Comparative Example 1 described below in smoothness and flavor. Although the step of crystal aging had been omitted, the shortening can be said to enjoy the effects of forming moderate crystals with excellent texture, accelerating such crystallization, and minimizing reduction of flavor by the emulsifier.

COMPARATIVE EXAMPLE 1

Production of Comparative Shortening

An oil phase consisting of 30 parts of palm oil, 50 parts of hydrogenated palm oil, 20 parts of rapeseed oil, and 0.3 parts of lecithin was melted at 70° C., stirred in a homomixer at a high rotational speed for 2 minutes, rapidly cooled for plasticization, and cooled to 5° C. to obtain shortening. The resulting shortening was evaluated for smoothness and flavor. The results obtained are shown in Table 2, which prove the resulting shortening to be much inferior in flavor.

EXAMPLE 24

Production of Margarine

A hundred parts of an edible fat and oil consisting of palm oil, hydrogenated palm oil, rapeseed oil, and a sorbitan fatty acid ester at a weight ratio of 30:50:20:0.3 was melted at 70° C. Eight parts of sample G was added thereto, and the mixture was left to stand at 65° C. for 30 minutes. A solution of 0.5 parts of defatted milk powder and 1 part of edible salt in 16 parts of hot water (70° C.) was slowly added to the mixture and mixed therewith while stirring in a homomixer. Then, the mixture was rapidly cooled for plasticization, maintained at 25° C. overnight, and cooled to 5° C. to give margarine according to the present invention (β-glucan content: 3.2%). The β-glucan was found uniformly dispersed. The resulting margarine was evaluated for stability, smoothness, and flavor. The results are shown in Table 1. The resulting margarine had a fine and smooth texture. Besides, the margarine was more flavorful than that of Comparative Example 2 described later, proving the effect of suppressing a reduction in flavor by the emulsifier.

EXAMPLE 25

Production of Margarine

A hundred parts of an edible fat and oil consisting of palm oil, hydrogenated palm oil, rapeseed oil, and a sorbitan fatty acid ester at a weight ratio of 30:50:20:0.3 was melted at 70° C. Eight parts of sample H was added thereto, and the mixture was left to stand at 65° C. for 30 minutes. A solution of 0.5 parts of defatted milk powder and 1 part of edible salt in 16 parts of hot water (70° C.) was slowly added to the mixture and mixed therewith while stirring in a homomixer. Then, the mixture was rapidly cooled for plasticization, maintained at 25° C. overnight, and cooled to 5° C. to give margarine according to the present invention (β-glucan content: 2.7%). The β-glucan was found uniformly dispersed. The resulting margarine was evaluated for stability, smoothness, and flavor. The results are shown in Table 1. The resulting margarine had a fine and smooth texture. Besides, the margarine was more flavorful than that of Comparative Example 2 described later, proving the effect of suppressing a reduction in flavor by the emulsifier.

EXAMPLE 26

Production of Margarine

A hundred parts of an edible fat and oil consisting of palm oil, hydrogenated palm oil, rapeseed oil, and a sorbitan fatty acid ester at a weight ratio of 30:50:20:0.3 was melted at 70° C. Eight parts of sample K was added thereto, and the mixture was left to stand at 65° C. for 30 minutes. A solution of 0.5 parts of defatted milk powder and 1 part of edible salt in 16 parts of hot water (70° C.) was slowly added to the mixture and mixed therewith while stirring in a homomixer. Then, the mixture was rapidly cooled for plasticization, maintained at 25° C. overnight, and cooled to 5° C. to give margarine according to the present invention ($\beta$-glucan content: 3.8%). The $\beta$-glucan was found uniformly dispersed. The resulting margarine was evaluated for stability, smoothness, and flavor. The results are shown in Table 1. The resulting margarine had a fine and smooth texture. Besides, the margarine was more flavorful than that of Comparative Example 2 below, proving the effect of suppressing a reduction in flavor by the emulsifier.

COMPARATIVE EXAMPLE 2

Production of Comparative Margarine

A hundred parts of an edible fat and oil consisting of palm oil, hydrogenated palm oil, rapeseed oil, and a sorbitan fatty acid ester at a weight ratio of 30:50:20:0.3 was melted at 70° C. A solution of 0.5 parts of defatted milk powder and 1 part of edible salt in 16 parts of hot water (70° C.) was slowly added to the mixture and mixed therewith while stirring in a homomixer. Then, the mixture was rapidly cooled for plasticization, maintained at 25° C. overnight and cooled to 5° C. to obtain margarine. The resulting margarine was evaluated for stability, smoothness, and flavor. The results are shown in Table 2.

EXAMPLE 27

Production of Dressing

Ten parts of sample G, 10 parts of egg yolk, 1.5 parts of edible salt, 11 parts of vinegar, 2.5 parts of soft white sugar, 0.05 parts of mustard powder, and 0.05 parts of onion powder were mixed by agitating in a mixer at a high speed for 5 minutes to prepare an aqueous phase. While the aqueous phase was further agitated in a homomixer at a high speed, 75 parts of soybean salad oil heated to 70° C. was slowly added thereto and mixed. The mixture was left to stand at 50° C. for 10 minutes, emulsified, and cooled at 5° C. for 24 hours to obtain a dressing ($\beta$-glucan content: 4.5%) according to the present invention. The $\beta$-glucan was found uniformly dispersed. The resulting dressing was evaluated for stability and flavor. The results are shown in Table 1. The resulting dressing was proved excellent in stability and flavor.

COMPARATIVE EXAMPLE 3

Production of Comparative Dressing

Ten parts of egg yolk, 1.5 parts of edible salt, 11 parts of vinegar, 2.5 parts of soft white sugar, 0.05 parts of mustard powder, and 0.05 parts of onion powder were mixed by stirring in a mixer at a high speed for 5 minutes to prepare an aqueous phase. A dressing was prepared by using the aqueous phase in the same manner as in Example 27. The resulting dressing was evaluated for stability and flavor. The results are shown in Table 2.

EXAMPLE 28

Production of Dressing

Ten parts of egg yolk, 1.5 parts of edible salt, 11 parts of vinegar, 2.5 parts of soft white sugar, 0.05 parts of mustard powder, and 0.05 parts of onion powder were mixed by agitating in a mixer at a high speed for 5 minutes to prepare an aqueous phase. While the aqueous phase was further agitated in a homomixer at a high speed, 75 parts of the $\beta$-glucan-containing fat and oil composition-12 of Example 12 was slowly added thereto and mixed. The mixture was emulsified and cooled at 5° C. for 24 hours to obtain a dressing ($\beta$-glucan content: 1.65%) according to the present invention. The $\beta$-glucan was found uniformly dispersed. The resulting dressing was evaluated for stability and flavor. The results are shown in Table 1. The resulting dressing was proved excellent in stability and flavor.

COMPARATIVE EXAMPLE 4

Production of Comparative Dressing

Ten parts of egg yolk, 1.5 parts of edible salt, 11 parts of vinegar, 2.5 parts of soft white sugar, 0.05 parts of mustard powder, and 0.05 parts of onion powder were mixed by agitating in a mixer at a high speed for 5 minutes to prepare an aqueous phase. While the aqueous phase was further agitated in a homomixer at a high speed, 75 parts of mixed fats and oils (40 parts of rice oil, 20 parts of olive oil, and 35 parts of safflower oil) was slowly added thereto and mixed. The mixture was emulsified and cooled at 5° C. for 24 hours to obtain a dressing. The resulting dressing was evaluated for stability and flavor. The results are shown in Table 2.

EXAMPLE 29

Production of Mayonnaise

Thirty parts of soybean salad oil was added to 30 parts of sample H, and the mixture was agitated for preliminary emulsification to prepare a $\beta$-glucan-containing fat and oil composition according to the present invention. A thoroughly agitated mixture consisting of 9 parts of egg yolk, 5.2 parts of starch, 8.2 parts of sugar, 2.8 parts of edible salt, 8 parts 10 of vinegar, 1 part of seasoning spices, and 6 parts of water was added to the fat and oil composition, and the mixture was emulsified in a colloid mill to make mayonnaise ($\beta$-glucan content: 12.6%) according to the present invention. The $\beta$-glucan was found uniformly dispersed. The mayonnaise was evaluated for stability, smoothness, and flavor. The results obtained are shown in Table 1. The resulting mayonnaise underwent no phase separation of water when stored for 1 month and had a smooth texture and a very good flavor.

COMPARATIVE EXAMPLE 5

Production of Comparative Mayonnaise

Thirty parts of soybean salad oil was added to 30 parts of water, and the mixture was agitated for preliminary emulsification to prepare a fat and oil composition. A thoroughly stirred mixture consisting of 9 parts of egg yolk, 5.2 parts of starch, 8.2 parts of sugar, 2.8 parts of edible salt, 8 parts of vinegar, 1 part of seasoning spices, and 6 parts of water was added to the fat and oil composition, and the mixture was emulsified in a colloid mill to prepare mayonnaise, which was evaluated for stability, smoothness and flavor. The results obtained are shown in Table 2.

EXAMPLE 30

Production of Mayonnaise

Nine parts of egg yolk, 8.2 parts of sugar, 2.8 parts of edible salt, 8 parts of vinegar, 1 part of seasoning spices, and 36 parts of sample B were mixed to prepare an aqueous phase. To the aqueous phase were added 25 parts of rapeseed oil and 10 parts of the β-glucan-containing fat and oil composition-3 of Example 3. The mixture was preliminarily emulsified by agitating and then further emulsified in a colloid mill to obtain mayonnaise (β-glucan content: 5.5%) according to the present invention. The β-glucan was found uniformly dispersed. The resulting mayonnaise was evaluated for stability, smoothness, and flavor. The results are shown in Table 1. The resulting mayonnaise underwent no separation of water when stored for 1 month and had a smooth texture and a very good flavor.

COMPARATIVE EXAMPLE 6

Production of Comparative Mayonnaise

Nine parts of egg yolk, 8.2 parts of sugar, 2.8 parts of edible salt, 8 parts of vinegar, 1 part of seasoning spices, and 36 parts of water were mixed to prepare an aqueous phase. To the aqueous phase were added 25 parts of rapeseed oil and 10 parts of palm oil. The mixture was preliminarily emulsified by agitating and then further emulsified in a colloid mill to obtain mayonnaise. The resulting mayonnaise was evaluated for stability, smoothness, and flavor. The results are shown in Table 2.

EXAMPLE 31

Production of Fat Spread

A mixture consisting of 27.6 parts of hydrogenated fish oil (melting point: 36° C.), 18.4 parts of cotton seed oil, 40 parts of sample K, 12.3 parts of water, 1 part of edible salt, 0.5 parts of defatted milk powder, 0.2 parts of flavor, and 0.3 parts of lecithin was emulsified and rapidly cooled for plasticization to prepare fat spread of the present invention (β-glucan content: 24%). The resulting fat spread was evaluated for stability, smoothness and flavor. The results are shown in Table 1. The resulting fat spread underwent no separation of water when stored for 1 month and had a smooth texture and a very good flavor.

COMPARATIVE EXAMPLE 7

Production of Comparative Fat Spread

A mixture consisting of 27.6 parts of hydrogenated fish oil. (melting point: 36° C.), 18.4 parts of cotton seed oil, 52.3 parts of water, 1 part of edible salt, 0.5 parts of defatted milk powder, 0.2 parts of flavor, and 0.3 parts of lecithin was emulsified and rapidly cooled for plasticization to prepare fat spread. The resulting fat spread was evaluated for stability, smoothness and flavor for comparison. The results are shown in Table 2.

EXAMPLE 32

Production of Roux Type Curry Sauce Mix

Forty-four parts of wheat flour (cake flour) and 34 parts of the shortening obtained in Example 22 were pan-fried brown, and the resulting roux was mixed with 8 parts of a commercially available curry powder mix to obtain a curry sauce mix (β-glucan content: 0.95%) according to the present invention. The β-glucan was found uniformly dispersed.

EXAMPLE 33

Making of Cookies

Fifty parts of β-glucan-containing fat and oil composition-9 obtained in Example 9 and 50 parts of soft white sugar were kneaded into cream in a hobart mixer at a high speed for 6 minutes. A mixture of 15 parts net of whole eggs, 1 part of edible salt, and 0.5 parts of ammonium hydrogencarbonate was added thereto, followed by mixing at a medium speed for 30 seconds. A hundred parts of sieved wheat flour was added, followed by mixing at a low speed for 30 seconds to prepare dough. The dough was put into a cylinder of 6 cm in diameter, pressed out by 1 cm, and cut. The cut pieces of the dough were baked at 200° C. for 13 minutes to obtain cookies (β-glucan content: 4.6%) according to the present invention. The β-glucan was found uniformly dispersed. The cookies were evaluated for firmness and flavor. The results are shown in Table 1.

COMPARATIVE EXAMPLE 8

Making of Comparative Cookies

Fifty parts of a fat and oil mixture (30 parts of palm olein oil, 70 parts of rapeseed oil, and 0.2 parts of protease-hydrolyzed egg yolk) and 50 parts of soft white sugar were kneaded into cream in a hobart mixer at a high speed for 6 minutes. To the cream was added a mixture of 15 parts net of whole eggs, 1 part of edible salt, and 0.5 parts of ammonium hydrogencarbonate was added thereto, followed by mixing at a medium speed for 30 seconds. The resulting mixture was further processed in the same manner as in Example 33 to make cookies. The cookies were evaluated for firmness and flavor. The results are shown in Table 2.

EXAMPLE 34

Making of Cookies

Fifty parts of β-glucan-containing fat and oil composition-14 obtained in Example 14 and 40 parts of soft white sugar were kneaded into cream in a hobart mixer at a high speed for 6 minutes. Twenty parts of raisin paste was added thereto, followed by mixing at a medium speed for 30 seconds. Sieved millet powder was added, followed by mixing at a low speed for 30 seconds to prepare dough. The dough was put into a cylinder of 6 cm in diameter, pressed out by 1 cm, and cut. The cut pieces of the dough were baked at 160° C. for 15 minutes to obtain cookies (β-glucan content: 2.5%) according to the present invention. The β-glucan was found uniformly dispersed. The cookies were evaluated for firmness and flavor. The results are shown in Table 1. While containing neither egg nor dairy products, the cookies had satisfactory texture.

COMPARATIVE EXAMPLE 9

Making of Comparative Cookies

A mixture of 20 parts of hydrogenated soybean oil (melting point: 45° C.), 35 parts of palm oil, 30 parts of cotton seed oil, and 0.2 parts of soybean lysolecithin was allowed to stand at 70° C. for 10 minuets, emulsified in a high-speed mixer, and rapidly cooled for plasticization to prepare a fat and oil composition showing margarine-like physical properties. Fifty parts of the resulting fat and oil composition and 40 parts of soft white sugar were kneaded into cream in a hobart mixer at a high speed for 6 minutes. Twenty parts of raisin paste was added thereto, followed by mixing at a medium speed for 30 seconds. The resulting mixture was further processed in the same manner as in Example 34 to make cookies. The cookies were evaluated for firmness and flavor. The results of evaluation are shown in Table 2.

EXAMPLE 35

Production of Chocolate

Twelve parts of cacao mass, 45 parts of powdered sugar, 20 parts of whole milk powder, 13 out of 23 parts of cacao butter, and 2 parts of sample G were put into a hobart mixer and mixed with a beater at a medium speed for 3 minutes. The mixture was rolled and conched to prepare a β-glucan-containing fat and oil composition (β-glucan content: 1%) according to the present invention. As observed with the naked eye, the β-glucan was found uniformly dispersed in the composition. The rest of cacao butter was added thereto and mixed to obtain chocolate mass. The chocolate mass was subjected to tempering, poured into a mold, and cooled down to obtain chocolate of the present invention, which was evaluated for smoothness, firmness, and flavor. The results obtained are shown in Table 1. The resulting chocolate had good melt in the mouth and a good flavor.

COMPARATIVE EXAMPLE 10

Production of Comparative Chocolate

Twelve parts of cacao mass, 45 parts of powdered sugar, 20 parts of whole milk powder, 13 out of 23 parts of cacao butter, and 2 parts of a fat and oil mixture (30 parts of palm olein oil, 70 parts of rapeseed oil, and 0.2 parts of protease-treated egg yolk) were put into a hobart mixer and mixed with a beater at a medium speed for 3 minutes. The mixture was rolled and conched to prepare a fat and oil composition. The rest of cacao butter was added thereto and mixed to obtain chocolate mass, which was further processed in the same manner as in Example 35 to make chocolate. The resulting chocolate was evaluated for smoothness, firmness, and flavor. The results obtained are shown in Table 2.

EXAMPLE 36

Production of Chocolate

Twelve parts of cacao mass, 45 parts of powdered sugar, 20 parts of whole milk powder, 23 parts of cacao butter, and 20 parts of β-glucan-containing fat and oil composition-4 obtained in Example 4 were put into a hobart mixer and mixed with a beater at a medium speed for 3 minutes. The mixture was rolled and conched to prepare chocolate mass. The chocolate mass was subjected to tempering, poured into a mold, and cooled to obtain chocolate of the invention (β-glucan content: 15%). The β-glucan was found uniformly dispersed in the chocolate. The resulting chocolate was evaluated for smoothness, firmness, and flavor. The results obtained are shown in Table 1. The chocolate had good melt in the mouth and a good flavor.

COMPARATIVE EXAMPLE 11

Production of Comparative Chocolate

Twelve parts of cacao mass, 45 parts of powdered sugar, 20 parts of whole milk powder, 23 parts of cacao butter, and 20 parts of palm oil were put into a hobart mixer and processed in the same manner as in Example 36 to make chocolate. The resulting chocolate was evaluated for smoothness, firmness, and flavor. The results obtained are shown in Table 2.

EXAMPLE 37

Production of Bread

Bread was made by using the β-glucan-containing margarine obtained in Example 26. A hundred parts of wheat flour, 3 parts of yeast, 4 parts of sugar, 2 parts of edible salt, 6 parts of the margarine obtained in Example 26, and 60 parts of water were mixed in a hopper mixer at a mixing temperature of 28° C. at a low speed for 2 minutes and then at a high speed for 4 minutes to prepare bread dough. The dough was allowed to ferment at 28° C. for 60 minutes and divided into 450 g portions, which were each formed into a ball and allowed to prove at 28° C. for 20 minutes. The dough was passed through a sheeter three times, shaped, put into a one-loaf pan, and finally proofed at 38° C. and 90% RH until it rose 2 cm above the lip of the pan. The final proofing took 42 minutes. The proofed dough was baked at 220° C. for 23 minutes to obtain a loaf of bread (β-glucan content: 0.16%) according to the present invention. The β-glucan was found uniformly dispersed throughout the bread. The resulting bread was evaluated for firmness and flavor. The results obtained are shown in Table 1. The resulting bread had softness, good volume and a satisfactory texture.

COMPARATIVE EXAMPLE 12

Production of Comparative Bread

Bread was made in the same manner as in Example 26, except for replacing the margarine obtained in Example 26 with margarine prepared in the same manner as in Example 26 but using no β-glucan (sample K). The resulting bread was evaluated for firmness and flavor. The results are shown in Table 2.

EXAMPLE 38

Production of Bread

A hundred parts of wheat flour, 3 parts of yeast, 4 parts of sugar, 2 parts of edible salt, 2 parts of the β-glucan-containing fat and oil composition-19 obtained in Example 19, 4 parts of shortening, 30 parts of sample B, and 33 parts of water were mixed in a hopper mixer at a mixing temperature of 28° C. at a low speed for 2 minutes and then at a high speed for 4 minutes to prepare bread dough. The dough was allowed to ferment at 28° C. for 60 minutes and divided into 450 g portions, which were each formed into a ball and allowed to prove at 28° C. for 20 minutes. The dough was passed through a sheeter three times, shaped, put into a one-loaf pan, and finally proofed at 38° C. and 90% RH until it rose 2 cm above the lip of the pan. The final proofing took 46 minutes. The proofed dough was baked at 210° C. for 30 minutes to obtain a loaf of bread (β-glucan content: 2.5%) according to the present invention. The β-glucan was found uniformly dispersed throughout the bread. The resulting bread was evaluated for firmness and flavor. The results obtained are shown in Table 1. The resulting bread had softness, good volume and a satisfactory texture.

COMPARATIVE EXAMPLE 13

Production of Comparative Bread

A hundred parts of wheat flour, 3 parts of yeast, 4 parts of sugar, 2 parts of edible salt, 2 parts of a powdered fat and oil composition prepared in the same manner as in Example 19 except for using no β-glucan (sample G), 4 parts of shortening, and 63 parts of water were mixed in a hopper mixer at a mixing temperature of 28° C. at a low speed for 2 minutes and then at a high speed for 4 minutes to prepare bread dough. The dough was further processed in the same manner as in Example 38 to obtain a loaf of bread. The bread was evaluated for firmness and flavor. The results are shown in Table 2.

EXAMPLE 39

Production of Boiled Rice

Japonica rice cultivar Koshihikari produced in Niigata, Japan was washed well with water. To 100 parts of washed rice were added 60 parts of water and 4 parts of the β-glucan-containing fat and oil composition-3 obtained in Example 3. The rice was boiled in an electric rice cooker to obtain boiled rice of the present invention (β-glucan content: 0.51%). The β-glucan was found uniformly distributed. The boiled rice was evaluated for firmness. The results are shown in Table 1. The resulting boiled rice had a light and soft texture.

COMPARATIVE EXAMPLE 14

Production of Comparative Boiled Rice

Japonica rice cultivar Koshihikari produced in Niigata, Japan was washed well with water. To 100 parts of washed rice were added 60 parts of water and 4 parts of soybean oil. The rice was boiled in an electric rice cooker to obtain boiled rice, which was evaluated for firmness. The results are shown in Table 2.

EXAMPLE 40

Production of Popcorn

Into a pan were put 100 parts of popcorn kernels, 2 parts of edible salt, and 10 parts of the β-glucan-containing fat and oil composition-10 obtained in Example 10, and the pan covered with a lid was heated on fire to make popcorn (β-glucan content: 0.38%) of the present invention. The β-glucan was found uniformly distributed. The resulting popcorn was evaluated for smoothness. The results are shown in Table 1. The popcorn had a smooth and light texture.

EXAMPLE 41

Production of Tofu

Tofu was made by using the shortening prepared in Example 22. A hundred parts of soybeans having been soaked in water was ground together with 140 parts of water, boiled at 100° C. for 5 minutes, transferred into a cotton bag, and squeezed to obtain soy milk. To the soy milk were added 3 parts of a coagulant (calcium sulfate) and 10 parts of the shortening obtained in Example 22. The mixture was gently stirred, coagulated at 75° C., and poured into a strainer lined with cotton cloth, left to stand for 30 minutes to obtain tofu (β-glucan content: 0.095%) according to the present invention. The β-glucan was found uniformly dispersed. The resulting tofu was evaluated for smoothness and flavor. The results are shown in Table 1. The resulting tofu had a good texture.

COMPARATIVE EXAMPLE 15

Production of Comparative Tofu

A hundred parts of soaked soybeans was ground together with 140 parts of water, boiled at 100° C. for 5 minutes, transferred into a cotton bag, and squeezed to obtain soy milk. To the soy milk were added 3 parts of a coagulant (calcium sulfate) and 10 parts of shortening prepared in the same manner as in Example 22 except for using no β-glucan (sample G). The mixture was gently stirred, coagulated at 75° C., and poured into a strainer lined with cotton cloth, left to stand for 30 minutes to obtain tofu. The resulting tofu was evaluated for smoothness and flavor. The results are shown in Table 2.

EXAMPLE 42

Production of Soft Chocolate

A mixture consisting of 50 parts of sugar, 5 parts of cacao mass, 15 parts of whole fat milk powder, 30 parts of the fat and oil composition-4 obtained in Example 4, 0.3 pails of lecithin, and 0.04 parts of vanillin was subjected to rolling and conching in a usual manner to obtain soft chocolate (β-glucan content: 13.5%) according to the present invention. The β-glucan was found uniformly dispersed. The resulting soft chocolate was evaluated for smoothness, firmness, and flavor. The results obtained are shown in Table 1. The resulting soft chocolate underwent no blooming and had a good flavor.

COMPARATIVE EXAMPLE 16

Production of Comparative Soft Chocolate

A mixture consisting of 50 parts of sugar, 5 parts of cacao mass, 15 parts of whole fat milk powder, 30 parts of palm oil, 0.3 parts of lecithin, and 0.04 parts of vanillin was subjected to rolling and conching in a usual manner to obtain soft chocolate, which was evaluated for smoothness, firmness, and flavor. The results obtained are shown in Table 2.

EXAMPLE 43

Production of Water-Free Cream

Thirty-five parts of the shortening prepared in Example 23, 45 parts of sugar, 10 parts of a tasty powder, and 10 parts of milk powder were mixed to obtain water-free cream (β-glucan content: 1%) according to the present invention. The β-glucan was found uniformly dispersed. The resulting water-free cream was evaluated for smoothness and flavor. The results are shown in Table 1. The water-free cream had good melt in the mouth and a very good flavor.

COMPARATIVE EXAMPLE 17

Production of Comparative Water-Free Cream

Thirty-five parts of shortening prepared in the same manner as in Example 23 except for using no β-glucan (sample K), 45 parts of sugar, 10 parts of a tasty powder, and 10 parts of milk powder were mixed to obtain water-free cream, which was evaluated for smoothness and flavor. The results are shown in Table 2.

EXAMPLE 44

Production of Whipped Cream for Cream Sandwiches

A mixture of 100 parts of the shortening prepared in Example 23 and 0.1 parts of a monoglyceride was beaten into whipped cream having a specific gravity of 0.3. A hundred parts of sugar syrup was added, and the cream was further beaten to prepare whipped cream having a specific gravity of 0.65 (β-glucan content: 1.45%), which was for cream sandwiches. The β-glucan was found uniformly dispersed. The whipped cream was evaluated for smoothness and flavor. The results are shown in Table 1. The resulting whipped cream had a very good flavor.

COMPARATIVE EXAMPLE 18

Production of Comparative Whipped Cream for Cream Sandwiches

Whipped cream for cream sandwiches was made in the same manner as in Example 44, except for using 100 parts of shortening prepared in the same manner as in Example 23 except for using no β-glucan (sample K). The resulting whipped cream was evaluated for smoothness and flavor. The results obtained are shown in Table 2.

EXAMPLE 45

Production of Hard Candy

Thirty-five parts of a fat and oil composition consisting of 100 parts of the β-glucan-containing fat and oil composition of Example 1, 100 parts of the β-glucan-containing fat and oil composition-6 of Example 6, 23 parts of a polyglycerol fatty acid ester, 14 parts of a glycerol fatty acid ester, and 4 parts of a sucrose fatty acid ester, 35 parts of sugar, 8.5 parts of thick malt syrup, 1.5 parts of defatted milk powder, and 40 parts of water were mixed into an oil-in-water emulsion. The emulsion was boiled down until the temperature reached 140° C. and further concentrated until the water content was reduced to 1.9%. The resulting thick syrup was cooled and molded to obtain hard candy according to the present invention (β-glucan content: 12.5%). The β-glucan was found uniformly dispersed. The resulting hard candy was evaluated for stability, smoothness, and flavor. The results are shown in Table 1. The resulting hard candy underwent no bleeding of oily components during storage and had a good flavor.

COMPARATIVE EXAMPLE 19

Production of Comparative Hard Candy

Thirty-five parts of a fat and oil composition consisting of 100 parts of soybean oil, 100 parts of palm oil, 23 parts of a polyglycerol fatty acid ester, 14 parts of a glycerol fatty acid ester, and 4 parts of a sucrose fatty acid ester, 35 parts of sugar, 8.5 parts of thick malt syrup, 1.5 parts of defatted milk powder, and 40 parts of water were mixed into an oil-in-water emulsion. The emulsion was boiled down until the temperature reached 140° C. and further concentrated to water content of 1.9%. The resulting thick syrup was cooled and molded to obtain hard candy. The resulting hard candy was evaluated for stability, smoothness, and flavor. The results are shown in Table 2.

EXAMPLE 46

Production of Whipped Cream

In 50 parts of water heated to 60° C. were dissolved 5 parts of defatted milk powder and 0.1 parts of sodium tripolyphosphate while stirring to prepare an aqueous phase. Separately, 10 parts of the β-glucan-containing fat and oil composition-3 of Example 3, 20 parts of the β-glucan-containing fat and oil composition-4 of Example 4, and 15 parts of the β-glucan-containing fat and oil composition-7 of Example 7 were mixed to prepare an oil phase. The oil phase was mixed with the aqueous phase by stirring to prepare a preliminary emulsion. The preliminary emulsion was homogenized under a pressure of 5 MPa, sterilized in a VTIS sterilization apparatus at 142° C. for 4 seconds, re-homogenized under a pressure of 5 MPa, cooled to 5° C., and then aged in a refrigerator for 24 hours to give whipped cream (β-glucan content: 13.6%) according to the present invention. The β-glucan was found uniformly dispersed. The resulting whipped cream was evaluated for stability, smoothness, and flavor. The results are shown in Table 1. The resulting whipped cream was proved to have satisfactory qualities of overrun, emulsion stability, heat resistant shape retention, flavor, melt-in-the-mouth, and shapability in piping into rosettes.

COMPARATIVE EXAMPLE 20

Production of Comparative Whipped Cream

In 50 parts of water heated to 60° C. were dissolved 5 parts of defatted milk powder and 0.1 parts of sodium tripolyphosphate while stirring to prepare an aqueous phase. Separately, 10 parts of soybean oil, 20 parts of palm oil, and 15 parts of rapeseed oil were mixed to prepare an oil phase. The oil phase was mixed with the aqueous phase by stirring to prepare a preliminary emulsion. The preliminary emulsion was further processed in the same manner as in Example 46 to obtain whipped cream, which was evaluated for stability and flavor. The results obtained are shown in Table 2.

EXAMPLE 47

Production of Milk Substitute Composition

In 64 parts of water heated to 60° C. were dissolved 25 parts of defatted milk powder, 0.2 parts of sodium hexametaphosphate, 0.2 parts of sodium citrate, and 0.3 parts of a sucrose fatty acid ester while stirring to prepare an aqueous phase. To the aqueous phase were added 10 parts of the β-glucancontaining fat and oil composition-17 of Example 17 and 0.3 parts of a glycerol fatty acid ester and mixed by stirring to prepare a preliminary emulsion. The preliminary emulsion was homogenized under a pressure of 5 MPa, sterilized in a VTIS sterilization apparatus at 142° C. for 4 seconds, re-homogenized under a pressure of 15 MPa, and cooled to 5° C. to obtain a milk substitute composition (β-glucan content: 2.2%) according to the present invention. The β-glucan was found uniformly dispersed. The milk substitute composition was evaluated for stability and flavor. The results are shown in Table 1. The resulting milk substitute composition was proved satisfactory in both flavor and emulsion stability.

COMPARATIVE EXAMPLE 21

Production of Comparative Milk Substitute Composition

In 64 parts of water heated to 60° C. were dissolved 25 parts of defatted milk powder, 0.2 parts of sodium hexametaphosphate, 0.2 parts of sodium citrate, and 0.3 parts of a sucrose fatty acid ester while stirring to prepare an aqueous phase. To the aqueous phase were added 10 parts of a fat and oil composition prepared in the same manner as in Example 17 except for adding no β-glucan (sample H) and 0.3 parts of a glycerol fatty acid ester and mixed by stirring to prepare a preliminary emulsion. The preliminary emulsion was further processed in the same manner as in Example 47 to give a milk substitute composition. The resulting milk substitute composition was evaluated for stability and flavor. The results are shown in Table 2.

EXAMPLE 48

Production of Food (Margarine) with Prophylactic Effects on Habitual Diseases

Ten parts of hydrogenated soybean oil (melting point: 45° C.), 35 parts of palm oil, 10 parts of the β-glucan-containing fat and oil composition-3 obtained in example 3, 30 parts of an interesterified oil containing at least 10% of plant sterol or plant sterol fatty acid esters, 13.3 parts of sample K, 1 part of edible salt, 0.5 parts of defatted milk powder, and 0.2 parts of flavor were emulsified and rapidly cooled for plasticization to make margarine having a cholesterol lowering effect (β-glucan content: 10%) according to the present invention. The β-glucan was found uniformly dispersed. The margarine having a cholesterol lowering effect was evaluated for smoothness and flavor. The results are shown in Table 1. The resulting margarine had good melt in the mouth and a good flavor.

COMPARATIVE EXAMPLE 22

Production of Comparative Food (Margarine) with Prophylactic Effects on Habitual Diseases Ten parts of hydrogenated soybean oil (melting point: 45° C.), 35 parts of palm oil, 10 parts of soybean oil, 30 parts of an interesterified oil containing at least 10% of plant sterol or plant sterol fatty acid esters, 13.3 parts of water, 1 part of edible salt, 0.5 parts of defatted milk powder, and 0.2 parts of flavor were emulsified and rapidly cooled for plasticization to make margarine having a cholesterol lowering effect, which was evaluated for smoothness and flavor. The results are shown in Table 2.

EXAMPLE 49

Production of Drug with Prophylactic Effects on Habitual Diseases

Three parts of high purity DHA (purity: 98%; POV: 1.0 meq/kg or less) containing 4000 ppm of α-tocopherol, 20 parts of sample K, and 10 parts of casein sodium were emulsified in a high-speed mixer in a nitrogen atmosphere and spray dried to prepare a powdered drug with prophylactic effects on habitual diseases (β-glucan content: 36.4%) according to the present invention. The β-glucan was found uniformly dispersed. The resulting drug with prophylactic effects on habitual diseases was evaluated for stability. The results are shown in Table 1. The POV of the drug was 0.8 meq/kg, proving the drug to be excellent in antioxidation stability.

COMPARATIVE EXAMPLE 23

Production of Comparative Drug with Prophylactic Effects on Habitual Diseases

Three parts of high purity DHA (purity: 98%; POV: 1.0 meq/kg or less) containing 4000 ppm of α-tocopherol, 20 parts of water, and 10 parts of casein sodium were emulsified in a high-speed mixer in a nitrogen atmosphere and spray dried to prepare a powdered drug with prophylactic effects on habitual diseases, which was evaluated for stability. The results are shown in Table 2. The POV of the resulting drug was 1.4 meq/kg, indicating inferior antioxidation stability.

In Examples and Comparative Examples described supra, stability and texture (smoothness, firmness, and flavor) of products were evaluated as follows. The mark "–" in Tables 1 and 2 indicates no evaluation made.

How to Evaluate the Stability

Stability was evaluated by visually inspecting for any change in appearance after 1 month storage at 5° C. and rated A to C according to the following standards.

<Evaluation Standards>

A: Excellent in stability.

B: Change in appearance, such as slight phase separation, observed.

C: Phase separation observed.

How to Evaluate the Texture

The texture was organoleptically evaluated by 10 panel members and rated A to C according to the following standards. The rating given to a sample by the greatest number out of 10 panel members was the rating of the sample.

<Evaluation Standards>

1) Smoothness

A: Very smooth

B: Smooth

C: Not smooth

2) Firmness

A: Very soft

B: Soft

C: Not soft

3) Flavor

A: Superior

B: Slightly inferior

C: Inferior

TABLE 1

| Example | Stability | Texture Smoothness | Texture Firmness | Flavor |
|---|---|---|---|---|
| 22 | — | A | — | A |
| 23 | — | A | — | A |
| 24 | A | A | — | A |
| 25 | A | A | — | A |
| 26 | A | A | — | A |
| 27 | A | — | — | A |
| 28 | A | — | — | A |
| 29 | A | A | — | A |
| 30 | A | A | — | A |
| 31 | A | A | — | A |
| 33 | — | — | A | A |
| 34 | — | — | A | A |
| 35 | — | A | A | A |
| 36 | — | A | A | A |
| 37 | — | — | A | A |
| 38 | — | — | A | A |
| 39 | — | — | A | — |
| 40 | — | A | — | — |
| 41 | — | A | — | A |
| 42 | — | A | A | A |
| 43 | — | A | — | A |
| 44 | — | A | — | A |
| 45 | A | A | — | A |
| 46 | A | A | — | A |
| 47 | A | — | — | A |
| 48 | — | A | — | A |
| 49 | A | — | — | — |

TABLE 2

| Compara. Example | Stability | Texture Smoothness | Texture Firmness | Flavor |
|---|---|---|---|---|
| 1 | — | B | — | C |
| 2 | A | A | — | B |
| 3 | B | — | — | B |
| 4 | B | — | — | A |
| 5 | C | A | — | B |
| 6 | C | B | — | B |
| 7 | B | A | — | B |
| 8 | — | — | B | B |
| 9 | — | — | B | B |
| 10 | — | A | B | B |
| 11 | — | A | B | B |
| 12 | — | — | B | A |
| 13 | — | — | B | A |
| 14 | — | — | B | — |
| 15 | — | A | — | B |
| 16 | — | A | B | C |
| 17 | — | A | — | C |
| 18 | — | A | — | C |
| 19 | B | A | — | B |
| 20 | B | — | — | C |
| 21 | B | — | — | B |
| 22 | — | B | — | C |
| 23 | C | — | — | — |

The novel microorganisms according to the present invention will then be described more specifically with reference to Examples. Test Examples 1 and 2 show screening for obtaining strains of the microorganisms. Test Examples 3 to 7 show the mycological properties of the strain ADK-34. Examples 50 to 52 demonstrate production of β-glucan using ADK-34. Analyses were conducted in the same manner as described supra in Analysis Examples 1 to 3.

TEST EXAMPLE 1

Strain Screening Method I

Microorganisms attaching to and growing on the surface of a broad range of commercially available foods that are usually eaten without cooking and mainly including Japanese traditional preserved foods were separated and screened to find β-glucan-producing strains. The screening method is described below.

A food (subject sample) was put in a sterilized petri dish, and 10 ml of sterilized PBS was added. The surface of the sample was repeatedly washed with the added PBS using a sterilized dropping pipette. The resulting washing was 10 to 100-fold diluted with sterilized PBS. A 200 μL portion of each dilution was put on an agar plate, spread with a spreader, and incubated at room temperature for two weeks. The agar plate was prepared by solidifying 20 ml of YM medium (Difco) containing 100 μg/ml of chloramphenicol and 1.5 wt % agar. Out of about 20,000 grown colonies those having the following properties were picked from the plate: those which were creamy white in the beginning of growth and gradually became glossy as a whole and wet; those which were wet and glossy as a whole with a slightly yellow to brown center or an yellow to brown edge; those assuming creamy white to pink as a whole; and those which gradually became greenish black and fuzzy. Colonies that were pink as a whole, non-glossy, and convex with non-spreading edge were excluded. The picked colonies were again incubated for 7 days for single strain isolation. Colonies that were found to have formed blastoconidia and/or shown yeast-like growth under microscopic observation were selected, and those observed to have conidiophores were screened out (results of first screening).

The strains obtained by the first screening were liquid-cultured. That is, each strain was cultured in YM medium containing 5 wt % sucrose at 26° for 4 days using a 24-well microplate. Those cultures which were viscous and in which the strain was uniformly dispersed were left (results of second screening).

A single strain isolated from the results of the second screening was inoculated into YM liquid medium and cultured at 26° C. for 96 hours. To the culture was added an equivalent amount of distilled water, and the culture was sterilized at 121° C. for 20 minutes and centrifuged at 8,000 rpm to obtain the supernatant liquid. To 30 μl of the liquid was added twice its volume of ethanol, followed by centrifugation at 1000 rpm for 10 minutes to separate into the precipitate and the medium. To the precipitate was added 100 μl of distilled water, and the total polysaccharide content was measured by the phenol-sulfuric acid method. The total polysaccharide content in the medium was also measured in the same manner. The cultures whose total polysaccharide content was higher in the precipitate than in the medium were judged positive. The strains judged positive are the results of third screening.

I The first screening of approximately 20,000 colonies grown from strains separated from subject samples gave 180 strains. The second screening resulted in isolation of 50 strains. The third screening provided 14 positives. The strains obtained by the third screening and three other strains purchased from Institute for Fermentation, Osaka, i.e., IFO-4466, IFO-6353, and IFO-7757 were each cultured to obtain their culture solutions. The β-glucan content of each culture solution was measured by the method taught in Analysis Example 1. The purity with respect to produced polysaccharide pullulan in the culture solution was also measured by the method shown in Analysis Example 3. The results obtained are shown in Table 3 below. The polysaccharide produced by ADK-34 was not digested by pullulanase, which indicates that the amount of the polysaccharide approximately agrees with the β-glucan content as determined. Namely, it was concluded that this strain produces β-glucan with high purity.

TABLE 3

| Strain | Absorbance (490 nm) | | Purity (%) | β-Glucan Content (mg/ml) |
|---|---|---|---|---|
| | Before Enzyme Treatment | After Enzyme Treatment | | |
| ADK-1 | 1.067 | 0.389 | 36.5 | 0.12 |
| ADK-4 | 1.183 | 0.504 | 42.6 | 0.23 |
| ADK-5 | 1.655 | 1.042 | 63 | 1.34 |
| ADK-6 | 1.364 | 0.764 | 56 | 0.649 |
| ADK-8 | 1.344 | 0.914 | 68 | 0.674 |
| ADK-10 | 1.469 | 0.646 | 44 | 0.357 |
| ADK-17 | 1.224 | 0.759 | 62 | 0.411 |
| ADK-20 | 1.003 | 0.552 | 55 | 0.264 |
| ADK-24 | 1.141 | 0.776 | 68 | 0.888 |
| ADK-27 | 1.225 | 0.882 | 72 | 0.954 |
| ADK-28 | 1.377 | 0.565 | 41 | 0.5 |
| ADK-31 | 1.419 | 0.426 | 30 | 0.311 |
| ADK-34 | 1.366 | 1.369 | 100 | 1.89 |
| ADK-42 | 1.154 | 0.427 | 37 | 0.44 |
| IFO-6353 | 1.455 | 0.757 | 52 | 0.743 |
| IFO-7757 | 0.975 | 0.722 | 74 | 0.684 |
| IFO-4466 | 0.736 | 0.521 | 71 | 0.701 |
| Pullulan 1 mg/ml | 0.755 | 0.016 | 3.9 | 0 |
| Pullulan 0.5 mg/ml | 0.411 | 0.009 | 2.2 | 0 |

TEST EXAMPLE 2

Strain Screening Method II

Strain screening was carried out in the same manner as in Test Example 1, except for using media containing 10 μg/ml of the antibiotic cycloheximide. As a result, the first screening of 4,000 colonies grown from strains separated from subject samples gave 30 strains. The second screening resulted in isolation of 10 strains. The third screening provided 3 positive strains (ADK-71, ADK-77, and ADK-82). The strains obtained by the third screening were tested in the same manner as in Test Example 1 to determine the β-glucan content and the purity with respect to the produced polysaccharide pullulan. The results obtained are shown in Table 4.

Furthermore, the three strains obtained by the third screening were identified through morphological characterization. The strains were each inoculated into YM agar medium and cultivated at 26° C. for 7 days. All the strains formed wholly glossy with a yellow pigmentation in the central portion and wet colonies. The plates were then stored at 4° C. for 7 days, whereupon the central yellow changed to blackish green. The colonies of ADK-71 and ADK-77 did not change in the area other than the central portion and remained white to pink. The colonies of ADK-82 turned black as a whole. Separately, when the three strains were each cultivated in YM liquid medium at 26° C. for 3 days, every strain was found to have formed blastoconidia and shown yeast-like growth under microscopic observation. In addition, the fungi of each of the three strains cultivated in YM agar medium at 26° C. for 7 days were observed to have developed chains of conidia but with no conidiophores. From these observations, the three strains were identified to be *Aureobasidium pullulans* species.

TABLE 4

| Strain | Absorbance (490 nm) | | Purity (%) | β-Glucan Content (mg/ml) |
|---|---|---|---|---|
| | Before Enzyme Treatment | After Enzyme Treatment | | |
| ADK-71 | 0.882 | 0.893 | 101 | 1.22 |
| ADK-77 | 0.741 | 0.842 | 114 | 0.936 |
| ADK-82 | 0.633 | 0.655 | 103 | 0.854 |
| Pullulan 1 mg/ml | 0.768 | 0.015 | 2 | 0 |
| Pullulan 0.5 mg/ml | 0.393 | 0.005 | 1.3 | 0 |

TEST EXAMPLE 3

Morphological and Cultural Properties

ADK-34, chosen from the strains obtained in Test Example 1, was cultured in YM medium (1 wt % glucose, 0.5 wt % peptone, 0.3 wt % yeast extract, 0.3 wt % malt extract; pH 6.0) at 26° C. for 3 days. Microscopic observation revealed the following. The cell size was 2 to 2.5 μm in width and 5 to 10 μm in length. The cells were colorless, oval, and smooth on the surface. No motility was observed. The hyphae were sparse, non-uniform, colorless, and smooth on the surface. The width of the hyphae was 2.5 μm. Formation of blastoconidia which was similar to yeast budding was observed.

TEST EXAMPLE 4

Agar Plate Cultivation

ADK-34, one of the strains obtained in Test Example 1, was cultured on a potato-dextrose-agar medium (Eiken) at 26° C. for 7 days. At day 3, the strain showed good growth, and the colonies were circular with a rough edge, glossy as a whole, smooth, and white. At day 5, the colonies were slightly grayish white with a smooth surface and showed yeast-like growth. At day 7, the surface of colonies turned pink. After 7 day cultivation at 26° C., the plate was refrigerated at 4° C. for 7 days, whereupon the pink pigmentation became slightly deeper but with no change of the individual colonies as a whole.

TEST EXAMPLE 5

Liquid Cultivation

ADK-34, one of the strains obtained in Test Example 1, was cultured in YM medium to examine the optimum growth temperature and pH. The optimum growth temperature was 26° C. The optimum growth pH was 5.0 to 7.0, the pH at the beginning of growth was 6.2, and the pH after the end of culturing was 7.5. A preferred growth temperature range was 20° to 30° C. The optimum growth temperature was 26° C. The permissible growth temperature range was 5° to 40° C. The strain decomposed hexoses such as glucose, fructose, and mannose, disaccharides such as sucrose, and starch. With any of these carbon sources the culture became viscous and had a specific aroma.

As a result of Test Examples 3 to 5, the ADK-34 strain, one of the microorganisms according to the present invention, was identified to be a strain belonging to the genus *Aureobasidium* from its mycological characteristics.

TEST EXAMPLE 6

Cycloheximide Resistance Test

The strains obtained by the screening in Test Examples 1 and 2 and IFO-4466, IFO-6353, and IFO-7757 purchased from Institute for Fermentation, Osaka, i.e., were tested for cycloheximide resistance as follows. Each strain was grown on YM agar medium (Difco) at 26° C. for 5 days. YM agar media (Difco) containing 5, 10, 20, 40, and 80 µg/ml of cycloheximide were prepared. The grown strain was inoculated into each of the cycloheximide-containing media using a sterile toothpick and incubated at 26° C. for 10 days. The plates were examined for colonies. The diameters of the colonies, if formed, were measured. The results are shown in Table 5.

TABLE 5

| (unit: mm)Strain | Cycloheximide Concentration (µg/ml) | | | | | |
|---|---|---|---|---|---|---|
| | 0 | 5 | 10 | 20 | 40 | 80 |
| ADK-1 | 16.5 | 0 | 0 | 0 | 0 | 0 |
| ADK-4 | 17.3 | 8.5 | 0 | 0 | 0 | 0 |
| ADK-5 | 15.6 | 6.3 | 0 | 0 | 0 | 0 |
| ADK-6 | 14.4 | 7.1 | 0 | 0 | 0 | 0 |
| ADK-8 | 16.8 | 7.7 | 1.1 | 0 | 0 | 0 |
| ADK-10 | 14.9 | 8.5 | 0 | 0 | 0 | 0 |
| ADK-17 | 12.7 | 6.7 | 0 | 0 | 0 | 0 |
| ADK-20 | 13.3 | 6.2 | 0 | 0 | 0 | 0 |
| ADK-24 | 15.6 | 9.1 | 2.5 | 0 | 0 | 0 |
| ADK-27 | 17.4 | 10.3 | 0 | 0 | 0 | 0 |
| ADK-28 | 15.4 | 7.1 | 0 | 0 | 0 | 0 |
| ADK-31 | 16.8 | 6.3 | 1.7 | 0 | 0 | 0 |
| ADK-34 | 15.5 | 13.6 | 6.7 | 5.1 | 3.7 | 0.5 |
| ADK-42 | 12.7 | 2.4 | 0 | 0 | 0 | 0 |
| ADK-71 | 13.7 | 7.6 | 4.1 | 1.8 | 1.2 | 0 |
| ADK-77 | 15.4 | 9.5 | 4.1 | 0.8 | 0 | 0 |
| ADK-82 | 16.8 | 10.4 | 2.9 | 1.5 | 1.2 | 0 |
| IFO-7757 | 17.5 | 0 | 0 | 0 | 0 | 0 |
| IFO-6353 | 15.6 | 7.3 | 2.3 | 0 | 0 | 0 |
| IFO-4466 | 14.8 | 4.4 | 0 | 0 | 0 | 0 |

As is apparent from Tables 3 and 5, IFO-4466, IFO-6353, and IFO-7757 do not have resistance to cycloheximide, and the β-glucan produced by them have low purity with respect to pullulan. It is obvious from Tables 3 to 5, on the other hand, that those isolates isolated front foods which are resistant to cycloheximide, i.e., ADK-34, ADK-71, ADK-77, and ADK-82 produce β-glucan with good purity with respect to pullulan and that many of those isolates which are not resistant to cycloheximide produce β-glucan but at low purity with respect to pullulan.

TEST EXAMPLE 7

Gene Analysis on 18S rRNA Gene

The sequence of 1732 base pairs of the 18S rRNA gene of ADK-34, obtained by the screening, was determined as follows. ADK-34 was shake-cultured in a potato-dextrose agar (Difco), and the culture was centrifuged. The solid was washed three times with distilled water to obtain fungi for DNA extraction. The fungi were cellularly disrupted using FastPrep FP120 (from Q-Biogene) and FastDNA-kit (from Q-Biogene), and genomic DNA was isolated using Dneasy Plant Mini Kit (from Qiagen). PCR amplification was carried out using the genomic DNA as a template, primers NS1 and NS8, and Ready-To-Go PCR Beads (Amersharm-Pharmasia Biotech).

The sequence (5'→3') of the primers NS1 and NS8 was GTAGTCATATGCTTGTCTC (NS1) and TCCGCAGGT-TCACCTACGGA (NS8), respectively. As a thermal cycler geneAmp PCR System 9600 (Applied Biosystems) was used. After completion of the PCR reaction, the PCR product was purified using QlAquick PCR Purification Kit (Qiagen). The resulting DNA fragment was subjected to direct sequencing reaction, and the base sequence was analyzed on ABI Prism 377 DNA Sequencer (Applied Biosystems). A DNA data base (DNA Data Bank of Japan, DDBJ) was searched for homologous sequences using the BLAST program.

The results of sequence analysis are shown in Sequence Listing, SEQ ID No. 1. The data base was searched based on the determined base sequence to examine homology between ADK-34 and homologous strains. The search results are shown in Tables 6 through 8. The determined base sequence (SEQ ID No. 1) and the results of the homology search (Tables 6 to 8) revealed 100% homology (perfect agreement) of ADK-34 with *Aureobasidium pullulans*. The present strain was thus identified to be *Aureobasidium pullulans*.

TABLE 6

| Sequences producing significant alignments: | (bits) | Value | |
|---|---|---|---|
| AY030322|AY030322.1 *Aureobasidium pullulans* 18S ribosomal RNA g . . . | 3433 | 0.0 | 1732/1732 (100%) |
| M55639|M55639.1 *Aureobasidium pullulans* 16S-like ribosomal RNA . . . | 3429 | 0.0 | 1731/1732 (99%) |
| U42474|U42474.1 *Dothidea insculpta* 18S small subunit ribosomal . . . | 3237 | 0.0 | 1699/1721 (98%) |
| U42475|U42475.1 *Dothidea hippophaeos* 18S small subunit ribosoma . . . | 3221 | 0.0 | 1691/1713 (98%) |
| U77668|U77668.1 *Coccodinium bartschii* 18S ribosomal RNA gene, p . . . | 3178 | 0.0 | 1690/1719 (98%) |
| AF258607|AF258607.1 *Scytalidium hyalinum* strain IP252699 18S ri . . . | 3158 | 0.0 | 1699/1733 (98%), |
| AF258606|AF258606.1 *Scytalidium hyalinum* strain IP151783 18S ri . . . | 3158 | 0.0 | 1699/1733 (98%), |
| AB041250|AB041250.1 *Phyllosticta pyrolae* gene for 18S rRNA, par . . . | 3158 | 0.0 | 1699/1733 (98%), |
| AB041249|AB041249.1 *Guignardia endophyllicola* gene for 18S rRNA . . . | 3150 | 0.0 | 1698/1733 (97%), |
| AB041248|AB041248.1 *Guignardia endophyllicola* gene for 18S rRNA . . . | 3150 | 0.0 | 1698/1733 (97%), |
| AB041247|AB041247.1 *Guignardia endophyllicola* gene for 18S rRNA . . . | 3150 | 0.0 | 1698/1733 (97%) |
| Y11716|Y11716.1 *P. dematioides* 18S rRNA gene. | 3148 | 0.0 | 1697/1732 (97%), |
| U42477|U42477.1 *Botryosphaeria ribis* 18S small subunit ribosoma . . . | 3144 | 0.0 | 1689/1722 (98%), |
| Y18702|Y18702.1 *Sarcinomyces petricola* 18S rRNA gene, strain CB . . . | 3108 | 0.0 | 1693/1733 (97%), |
| D49656|D49656.1 *Lasioderma serricorne* yeast-like symbiote DNA f . . . | 3102 | 0.0 | 1692/1733 (97%), |
| AJ224362|AJ224362.1 *Bulgaria inquinans* 18S rDNA. | 3094 | 0.0 | 1691/1733 (97%), |
| AF088239|AF088239.1 *Lecidea fuscoatra* 18S ribosomal RNA, partia . . . | 3033 | 0.0 | 1666/1710 (97%), |
| Y18693|Y18693.1 *Hortaea werneckii* 18S rRNA gene, strain CBS 107 . . . | 3027 | 0.0 | 1679/1731 (96%) |
| AF088253|AF088253.1 *Umbilicaria subglabra* 18S ribosomal RNA, pa . . . | 3015 | 0.0 | 1648/1689 (97%), |
| Y11355|Y11355.1 *S. crustaceus* 18S rRNA gene. | 3001 | 0.0 | 1674/1731 (96%), |
| U42478|U42478.1 *Sporormia lignicola* 18S small subunit ribosomal . . . | 2991 | 0.0 | 1665/1717 (96%) |
| AF184755|AF184755.1 *Metus conglomeratus* small subunit ribosomal . . . | 2991 | 0.0 | 1678/1733 (96%), |

TABLE 6-continued

| Sequences producing significant alignments: | | (bits) Value | |
|---|---|---|---|
| AB016175\|AB016175.1 *Euascomycetes* sp. K89 gene for 18S rRNA, pa . . . | 2958 | 0.0 | 1680/1733 (96%), |
| AF184753\|AF184753.1 *Cladonia rangiferina* small subunit ribosma . . . | 2976 | 0.0 | 1676/1733 (96%), |
| AF140236\|AF140236.1 *Stereocaulon paschale* small subunit ribosom . . . | 2976 | 0.0 | 1676/1733 (96%), |
| AB015778\|AB015778.1 *Pseudogymnoascus roseus* 18S rRNA gene, part . . . | 2972 | 0.0 | 1640/1687 (97%) |
| AF184756\|AF184756.1 *Pilophorus cereolus* small subunit ribosomal . . . | 2968 | 0.0 | 1675/1733 (96%), |
| AF184761\|AF184761.1 *Stereocaulon vesuvianum* small subunit ribos . . . | 2960 | 0.0 | 1674/1733 (96%), |
| AF184754\|AF184754.1 *Heterodea muelleri* small subunit ribosomal . . . | 2960 | 0.0 | 1674/1733 (96%), |
| AF168167\|AF168167.1 Dark septate endophyte DS16b 18S ribosomal . . . | 2960 | 0.0 | 1661/1713 (96%), |
| AF184757\|AF184757.1 *Pilophorus robustus* small subunit ribosomal . . . | 2952 | 0.0 | 1673/1733 (96%), |
| AF117984\|AF117984.1 *Hypogymnia physodes* nuclear small subunit r . . . | 2952 | 0.0 | 1665/1720 (96%), |
| AF088246\|AF088246.1 *Rhizocarpon geographicum* 18S ribosomal RNA . . . | 2946 | 0.0 | 1643/1693 (97%), |
| AF241544\|AF241544.1 *Cladonia sulphurina* small subunit ribosomal . . . | 2944 | 0.0 | 1672/1733 (96%), |
| AB015776\|AB015776.1 *Byssoascos striatosporus* 18S rRNA gene, par . . . | 2940 | 0.0 | 1636/1687 (96%) |

TABLE 7

| Sequences producing significant alignments: | | (bits) Value | |
|---|---|---|---|
| AF140233\|AF140233.1 *Alectoria sarmentosa* small subunit ribosoma . . . | 2938 | 0.0 | 1671/1733 (96%), |
| U70960\|U70960.1 *Pilophorus acicularis* 18S small subunit ribosom . . . | 2936 | 0.0 | 1671/1733 (96%), |
| AF085471\|AF085471.1 *Baeomyces rufus* 18S small subunit ribosomal . . . | 2932 | 0.0 | 1638/1691 (96%) |
| U70961\|U70961.1 *Stereocaulon ramulosum* 18S small subunit riboso . . . | 2928 | 0.0 | 1670/1733 (96%), |
| AF088238\|AF088238.1 *Lasallia rossica* 18S ribosomal RNA, partial . . . | 2926 | 0.0 | 1654/1708 (96%), |
| Y14210\|Y14210.1 *Monilinia laxa* 18S rRNA gene, exon 1. partial. | 2916 | 0.0 | 1636/1691 (96%) |
| U42476\|U42476.1 *Botryosphaeria rhodina* 18S small subunit riboso . . . | 2914 | 0.0 | 1619/1671 (96%), |
| U86692\|U86692.1 *Stenocybe pullatula* 18S SSU ribosomal RNA, part . . . | 2910 | 0.0 | 1640/1696 (96%), |
| AF117992\|AF117992.1 *Xanthoparmelia conspersa* nuclear small subu . . . | 2910 | 0.0 | 1664/1728 (96%), |
| AF085475\|AF085475.1 *Cladonia subcervicornis* 18S small subunit r . . . | 2910 | 0.0 | 1637/1692 (96%), |
| AF085465\|AF085465.1 *Stereocaulon taeniarum* 18S small subunit ri . . . | 2910 | 0.0 | 1634/1688 (96%), |
| AB015787\|AB015787.1 *Oidiodendron tenuissimum* 18S rRNA gene, iso . . . | 2910 | 0.0 | 1634/1688 (96%), |
| AF140235\|AF140235.1 *Cornicularia normoerica* small subunit ribos . . . | 2908 | 0.0 | 1663/1727 (96%), |
| AB015777\|AB015777.1 *Myxotrichum deflexum* 18S rRNA gene, isolate . . . | 2908 | 0.0 | 1632/1687 (96%) |
| AF184759\|AF184759.1 *Psora decipiens* small subunit ribosomal RNA . . . | 2904 | 0.0 | 1667/1733 (96%), |
| AF117981\|AF117981.1 *Neophyllis melacarpa* nuclear small subunit . . . | 2904 | 0.0 | 1667/1733 (96%), |
| AF088251\|AF088251.1 *Stereocaulon ramulosum* 18S ribosomal RNA, p . . . | 2904 | 0.0 | 1652/1713 (96%), |
| AF088245\|AF088245.1 *Pseudevernia cladoniae* 18S ribosomal RNA, p . . . | 2902 | 0.0 | 1638/1696 (96%), |
| AF201452\|AF201452.1 *Rhytidhysteron rufulum* 18S ribosomal RNA ge . . . | 2900 | 0.0 | 1578/1615 (97%), |
| AF274110\|AF274110.1 *Lepolichen coccophons* 18S ribosomal RNA ge . . . | 2898 | 0.0 | 1660/1725 (96%), |
| AF117991\|AF117991.1 *Pleurosricta acetabulum* nuclear small subun . . . | 2898 | 0.0 | 1664/1730 (96%), |
| U43463\|U43463.1 *Mycosphaerella mycopappi* small subunit nuclear . . . | 2894 | 0.0 | 1664/1732 (96%), |
| AF085466\|AF085466.1 *Stereocaulon vesuvianum* 18S small subunit r . . . | 2894 | 0.0 | 1632/1688 (96%), |
| AB033475\|AB033475.1 *Blumeria graminis* f. sp. *bromi* gene for 18S . . . | 2894 | 0.0 | 1660/1724 (96%), |
| U42485\|U42485.1 *Lophiostoma crenatum* 18S small subunit ribosoma . . . | 2892 | 0.0 | 1655/1719 (96%), |
| AF053726\|AF053726.1 *Kirschsteiniothelia maritima* small subunit . . . | 2890 | 0.0 | 1659/1726 (96%) |
| AF201455\|AF201455.1 *Tubeufia helicoma* 18S ribosomal RNA gene, p . . . | 2886 | 0.0 | 1586/1628 (97%), |
| AF241541\|AF241541.1 *Xanthoria parietina* small subunit ribosomal . . . | 2884 | 0.0 | 1653/1719 (96%), |
| U70959\|U70959.1 *Leifidium tenerum* 18S small subunit ribosomal R . . . | 2880 | 0.0 | 1664/1733 (96%), |
| AF282910\|AF282910.1 *Lichinella cribellifera* 18S small subunit r . . . | 2880 | 0.0 | 1667/1733 (96%), |
| AF117986\|AF117986.1 *Cetraria islandica* nuclear small subunit ri . . . | 2880 | 0.0 | 1646/1709 (96%), |
| L37540\|L37540.1 *Porpidia crustulata* (Ach.) Hertel and Knoph nuc . . . | 2878 | 0.0 | 1570/1608 (97%), |
| AF184751\|AF184751.1 *Cladia retipora* small subunit ribosomal RNA . . . | 2874 | 0.0 | 1636/1697 (96%), |

TABLE 8

| Sequences producing significant alignments: | | (bits) Value | |
|---|---|---|---|
| AF282913\|AF282913.1 *Peltula obscurans* 18S small subunit ribosom . . . | 2872 | 0.0 | 1663/1732 (96%), |
| AF085474\|AF085474.1 *Pycnothelia papillaria* 18S small subunit ri . . . | 2872 | 0.0 | 1618/1673 (96%), |
| AB033479\|AB033479.1 *Leveillula taurica* gene for 18S ribosomal RNA . . . | 2855 | 0.0 | 1654/1720 (96%), |
| AF117985\|AF117985.1 *Parmelia saxatilis* nuclear small subunit ri . . . | 2859 | 0.0 | 1653/1722 (95%), |
| AF088254\|AF088254.1 *Xanthoria elegans* 18S ribosomal RNA, partia . . . | 2865 | 0.0 | 1655/1724 (95%), |
| AF117988\|AF117988.1 *Usnea florida* nuclear small subunit ribosom . . . | 2853 | 0.0 | 1635/1699 (96%), |
| U42483\|U42483.1 *Herpotrichia juniperi* 18S small subunit ribosom . . . | 2847 | 0.0 | 1649/1720 (95%) |
| AF140234\|AF140234.1 *Alectoria ochroleuca* small subunit ribosoma . . . | 2847 | 0.0 | 1598/1652 (96%), |
| AF091587\|AF091587.1 *Scoliciosporum umbrimum* 18S ribosomal RNA, g . . . | 2847 | 0.0 | 1625/1688 (96%) |
| AF085469\|AF085469.1 *Pilophorus acicularis* 18S small subunit rib . . . | 2845 | 0.0 | 1613/1671 (96%), |
| AF010590\|AF010590.1 *Ascozonus woolhopensis* SSU ribosomal RNA, ge . . . | 2841 | 0.0 | 1654/1727 (95%), |
| AF117990\|AF117990.1 *Vulpicida juniperina* nuclear small subunit . . . | 2831 | 0.0 | 1624/1688 (96%), |
| Z30239\|Z30239.1 *S. flavida* gene for 18S ribosomal RNA. | 2819 | 0.0 | 1638/1711 (95%), |
| AB016174\|AB016174.1 *Geomyces pannorum* gene for 18S rRNA, partia . . . | 2809 | 0.0 | 1544/1588 (97%), |
| AB016173\|AB016173.1 *Geomyces asperulatus* gene for 18S rRNA, par . . . | 2809 | 0.0 | 1544/1588 (97%), |
| AF117987\|AF117987.1 *Evernia prunastri* nuclear small subunit rib . . . | 2807 | 0.0 | 1621/1688 (96%), |

TABLE 8-continued

| Sequences producing significant alignments: | | (bits) | Value |
|---|---|---|---|
| AF184749\|AF184749.1 | *Bunodophoron australe* small subunit ribosom . . . | 2805 | 0.0 1619/1687 (95%) |
| AF241540\|AF241540.1 | *Caloplaca flavorubescens* small subunit ribo . . . | 2795 | 0.0 1624/1694 (95%), |
| AF091583\|AF091583.1 | *Lecidella meiococca* 18S ribosomal RNA gene, . . . | 2795 | 0.0 1626/1697 (95%), |
| AF282914\|AF282914.1 | *Pterygiopsis guyanensis* 18S small subunit r . . . | 2771 | 0.0 1654/1734 (95%), |
| U72713\|U72713.1 | *Cladia aggregate* 18S small subunit ribosomal RN . . . | 2755 | 0.0 1597/1665 (95%), |
| AF091589\|AF091589.1 | *Lecania cyrtella* 18S ribosomal RNA gene, pa . . . | 2753 | 0.0 1635/1713 (95%), |
| AF085468\|AF085468.1 | *Allocetraria madreporiformis* 18S small subu . . . | 2732 | 0.0 1536/1592 (96%) |
| AF088250\|AF088250.1 | *Squamarina lentigera* 18S ribosomal RNA, par . . . | 2692 | 0.0 1623/1710 (94%), |
| AF201453\|AF201453.1 | *Aliquandostipite khaoyaiensis* 18S ribosomal . . . | 2684 | 0.0 1603/1684 (95%), |
| AF258605\|AF258605.1 | *Scytalidium dimidiatum* strain IP252899 18S . . . | 2615 | 0.0 1374/1391 (98%), |
| AF258604\|AF258604.1 | *Scytalidium dimidiatum* strain IP252799 18S . . . | 2615 | 0.0 1374/1391 (98%), |
| AF258603\|AF258603.1 | *Scytalidium dimidiatum* strain IP127881 18S . . . | 2615 | 0.0 1374/1391 (98%), |
| AB033477\|AB033477.1 | *Arthrocladiella mougeotii* gene for 18S ribo . . . | 2613 | 0.0 1418/1450 (97%), |
| U45438\|U45438.1 | *Amylocarpus encephaloides* small subunit rRNA gene . . . | 2605 | 0.0 1441/1481 (97%), |
| AF274113\|AF274113.1 | *Coccotrema pocillarium* 18S ribosomal RNA ge . . . | 2375 | 0.0 1351/1401 (96%), |
| AF184752\|AF184752.1 | *Cladonia gracilis* subsp. *turbinate* small su_ . . . | 2226 | 0.0 1239/1277 (97%), |

TEST EXAMPLE 8

ITS-5.8S rRNA Gene

The sequence of 563 or 564 base pairs of the ITS-5.8S rRNA gene of ADK-34 obtained by the screening, IFO-6353, and IFO-7757 was determined as follows. Each strain was shake-cultured in a potato-dextrose agar (Difco), and the culture was centrifuged and washed three times with distilled water to obtain fungi for DNA extraction. The fungi were cellularly disrupted using FastPrep FP120 (from Q-Biogene) and FastDNA-kit (from Q-Biogene), and genomic DNA was isolated using Dneasy Plant Mini Kit (from Qiagen). PCR amplification was carried out using the genomic DNA as a template, primers ITS5 and ITS4, and Realdy-To-Go PCR Beads (Amersharm-Pharmasia Biotech).

The sequence (5'→3') of the primers ITS4 and ITS 5 was TCCTCCGCTTATTGATATGC (ITS4) and GGAAG-TAAAAGTCGTAACAAGG (ITS5), respectively. As a thermal cycler geneAmp PCR System 9600 (Applied Biosystems) was used. After completion of the PCR reaction, the PCR product was purified using QIAquick PCR Purification Kit (Qiagen). The resulting DNA fragment was subjected to direct sequencing reaction, and the base sequence was analyzed on ABI Prism 377 DNA Sequencer (Applied Biosystems). A DNA data base (DNA Data Bank of Japan, DDBJ) was searched for homologous sequences using the BLAST program.

The results of ADK-34, IFO-6353, and IFO-7757 are shown in Sequence Listing, SEQ ID Nos. 2, 3, and 4, respectively. The data base was searched based on the determined base sequences to examine homology between these strains and their homologous strains. The search results are shown in Tables 9 and 10. On comparing the determined base sequences, ADK-34 was found different from either of IFO-6353 and IFO-7757 (not in complete agreement). The homology (similarity) between ADK-34 and IFO-6353 was 98%, and that between ADK-34 and IFO-7757 was 98%. The homology search results (Tables 9 and 10) indicated that (1) there is no report on a strain whose 563 bp in the ITS-5.8S region completely agree with those of ADK-34; (2) IFO-6353 showed 100% homology (perfect agreement) with the reported *Aureobasidium pullulans* strain, Accession No. AJ276062 (see Table 11); (3) IFO-7757 showed 99% homology with the reported *Aureobasidium pullulans* strain, Accession No. AJ276062 (see Table 12); and (4) the homology between ADK-34 and Accession No. AJ276062 was 98%.

From these results, ADK-34 was judged to be a new strain, differing from the reported *Aureobasidium pullulans* strains in part of the base sequence in the ITS-5.8S region.

TABLE 9

| Sequences producing significant alignments: | | (bits) | Value |
|---|---|---|---|
| AF013229\|AF013229.1 | *Aureobasidium pullulans* 18S ribosomal RNA g . . . | 997 | 0.0 555/567 (97%), |
| AY029406\|AY029406.1 | *Astasia longa* internal transcribed spacer 1 . . . | 989 | 0.0 538/546 (98%), |
| AJ276062\|AJ276062.1 | *Aureobasidium pullulans* 5.8S rRNA gene and . . . | 971 | 0.0 517/526 (98%) |
| AF121287\|AF121287.1 | *Aureobasidium pullulans* var. *melanigenum* st . . . | 971 | 0.0 507/510 (99%), |
| AJ244265\|AJ244265.1 | *Trimmatostroma abietina* 5.8S rRNA gene and . . . | 965 | 0.0 503/507 (99%), |
| AJ244231\|AJ244231.1 | *Aureobasidium pullulans* 5.8S rRNA gene and . . . | 965 | 0.0 503/507 (99%), |
| AJ244235\|AJ244235.1 | *Aureobasidium pullulans* 5.8S rRNA gene and . . . | 963 | 0.0 501/506 (99%) |
| AJ244234\|AJ244234.1 | *Aureobasidium pullulans* 5.8S rRNA gene and . . . | 963 | 0.0 501/506 (99%) |
| AF121285\|AF121285.1 | *Aureobasidium pullulans* strain ATCC48433 in . . . | 952 | 0.0 501/508 (98%) |
| AF121281\|AF121281.1 | *Aureobasidium pullulans* strain ATCC11942 in . . . | 952 | 0.0 501/508 (98%) |
| AJ244232\|AJ244232.1 | *Aureobasidium pullulans* 5.8S rRNA gene and . . . | 948 | 0.0 499/506 (98%) |
| AF182377\|AF182377.1 | *Hormonema* sp. F-054, 764 internal transcribe . . . | 940 | 0.0 501/510 (98%) |
| AF121284\|AF121284.1 | *Aureobasidium pullulans* strain ATCC42457 in . . . | 936 | 0.0 499/508 (98%) |
| AJ244233\|AJ244233.1 | *Aureobasidium pullulans* 5.8S rRNA gene and . . . | 934 | 0.0 492/499 (98%) |
| AJ244269\|AJ244269.1 | *Aureobasidium pullulans* 5.8S rRNA gene and . . . | 932 | 0.0 497/506 (98%) |
| AJ244236\|AJ244236.1 | *Aureobasidium pullulans* 5.8S rRNA gene and . . . | 932 | 0.0 497/506 (98%) |
| AF121286\|AF121286.1 | *Aureobasidium pullulans* var. *melanigenum* st . . . | 920 | 0.0 497/508 (97%) |
| AJ276061\|AJ276061.1 | *Aureobasidium pullulans* 5.8S rRNA gene and . . . | 914 | 0.0 497/505 (98%), |
| AJ244252\|AJ244252.1 | *Kabatiella lini* 5.8S rRNA gene and internal . . . | 906 | 0.0 496/508 (97%), |
| AJ244251\|AJ244251.1 | *Kabatiella canlivora* 5.8S rRNA gene and int . . . | 825 | 0.0 487/508 (95%), |

TABLE 9-continued

| Sequences producing significant alignments: | | (bits) | Value | |
|---|---|---|---|---|
| AF013225\|AF013225.1 *Phaeocryptopus gaeumannii* 18S ribosomal RNA . . . | 446 | e−124 | 361/398 | (90%), |
| AJ244257\|AJ244257.1 *Pringsheimia smilacis* 5.8S rRNA gene and in . . . | 428 | e−118 | 255/264 | (96%), |
| AJ244248\|AJ244248.1 *Hormonema prunorum* 5.8S rRNA gene and inter . . . | 420 | e−116 | 253/264 | (95%), |
| AJ244245\|AJ244245.1 *Dothiora rhamni-alpinae* 5.8S rRNA gene and . . . | 420 | e−116 | 252/264 | (95%) |
| AJ244242\|AJ244242.1 *Dothichiza pityophila* 5.8S rRNA gene and in . . . | 418 | e−115 | 246/255 | (96%), |
| AF182376\|AF182376.1 *Kabatina junipeni* internal transcribed spac . . . | 416 | e−115 | 251/262 | (95%), |
| AF182375\|AF182375.1 *Hormonema* sp. ATCC74360 internal transribe . . . | 416 | e−115 | 251/262 | (95%), |
| AJ244243\|AJ244243.1 *Dothiora cannabinae* 5.8S rRNA gene and inte . . . | 412 | e−113 | 252/264 | (95%), |
| AF027764\|AF027764.1 *Dothidea insculpta* CBS 189.58 18S ribosomal . . . | 412 | e−113 | 252/264 | (95%), |
| AF013226\|AF013226.1 *Kabatina thujae* 18S ribosomal RNA gene, par . . . | 412 | e−113 | 252/264 | (95%), |
| AF027763\|AF027763.1 *Dothidea hippophaeos* CBS 18658 18S ribosom . . . | 404 | e−111 | 251/264 | (95%), |
| AJ278930\|AJ278930.1 *Hormonema dematioides* 5.8S rRNA gene, 26S r . . . | 402 | e−110 | 244/255 | (95%), |
| AJ278929\|AJ278929.1 *Hormonema dematioides* 5.8S rRNA gene, 26S r . . . | 402 | e−110 | 244/255 | (95%), |
| AJ278928\|AJ278928.1 *Hormonema dematioides* 18S rRNA gene (partia . . . | 402 | e−110 | 244/255 | (95%), |
| AJ278927\|AJ278927.1 *Hormonema dematioides* 5.8S rRNA gene, 26S r . . . | 402 | e−110 | 244/255 | (95%), |

TABLE 10

| Sequences producing significant alignments: | | (bits) | Value | |
|---|---|---|---|---|
| AJ278926\|AJ278926.1 *Hormonema dematioides* 5.8S rRNA gene, 26S r . . . | 402 | e−110 | 244/255 | (95%), |
| AJ278925\|AJ278925.1 *Hormonema dematioides* 5.8S rRNA gene, 26S r . . . | 402 | e−110 | 244/255 | (95%), |
| AJ244262\|AJ244262.1 *Sydowia polyspora* 5.8S rRNA gene and intern . . . | 402 | e−110 | 244/255 | (95%), |
| AJ244247\|AJ244247.1 *Hormonema macrosporum* 5.8S rRNA gene and in . . . | 402 | e−110 | 244/255 | (95%), |
| AJ244244\|AJ244244.1 *Dothiora europaea* 5.8S rRNA gene and intern . . . | 402 | e−110 | 252/263 | (95%), |
| AF182378\|AF182378.1 *Hormonema* sp. F-054,258 internal transcribe . . . | 402 | e−110 | 240/251 | (95%), |
| AF013232\|AF013232.1 *Rhizosphaera kalkhoffii* 18S ribosomal RNA g . . . | 402 | e−110 | 244/255 | (95%), |
| AF013228\|AF013228.1 *Hormonema dematioides* 18S ribosomal RNA gen . . . | 402 | e−110 | 244/255 | (95%), |
| AF260224\|AF260224.1 *Kabatina juniperi* 18S ribosomal RNA, partia . . . | 396 | e−109 | 250/264 | (94%), |
| AF013231\|AF013231.1 *Rhizosphaera kalkhoffii* 18S ribosomal RNA g . . . | 389 | e−106 | 244/256 | (95%), |
| AF121283\|AF121283.1 *Aureobasidium pullulans* strain ATCC16629 in . . . | 379 | e−103 | 238/251 | (94%), |
| AF121282\|AF121282.1 *Aureobasidium pullulans* strain ATCC16628 in . . . | 379 | e−103 | 238/251 | (94%), |
| AF013230\|AF013230.1 *Rhizosphaera pini* 18S ribosomal RNA gene, p . . . | 375 | e−102 | 244/257 | (94%), |
| AF246930\|AF246930.1 *Botryosphaeria mamane* isolate 97-59 18S rib . . . | 359 | 2e−97 | 214/225 | (95%) |
| AF246929\|AF246929.1 *Botryosphaeria mamane* isolate 97-58 18S rib . . . | 359 | 2e−97 | 214/225 | (95%) |
| AF243410\|AF243410.1 *Sphaeropsis sapinea* isolate 215 18S ribosom . . . | 345 | 2e−93 | 214/226 | (94%) |
| AF243409\|AF243409.1 *Sphaeropsis sapinea* isolate 411 18S ribosom . . . | 345 | 2e−93 | 214/226 | (94%), |
| U28059\|U28059.1 *Sphaceloma fawcettii* 18S ribosomal RNA and 26S . . . | 339 | 1e−91 | 189/195 | (96%) |
| U28058\|U28058.1 *Elsinoe fawcettii* 18S ribosomal RNA and 26S rib . . . | 339 | 1e−91 | 189/195 | (96%) |
| AF297232\|AF297232.1 *Cercospora sorghi f. maydis* Kenya 1 18S rib . . . | 335 | 2e−90 | 187/193 | (96%) |
| AF297230\|AF297230,1 *Cercospora nicotianae* 18S ribosomal RNA gen . . . | 335 | 2e−90 | 187/193 | (96%) |
| AF297229\|AF297229.1 *Cercospora asparagi* 18S ribosomal RNA gene . . . | 335 | 2e−90 | 187/193 | (96%) |
| AF243394\|AF243394.1 *Botryosphaeria ribis* isolate 968 18S ribos . . . | 335 | 2e−90 | 212/225 | (94%), |
| AF243393\|AF243393.1 *Botryosphaeria ribis* isolate 94-128 18S rib . . . | 335 | 2e−90 | 212/225 | (94%), |
| AF079776\|AF079776.1 *Phomopsis amaranthicola* 18S ribosomal RNA g . . . | 335 | 2e−90 | 187/193 | (96%) |
| AB041245\|AB041245.1 *Guignardia laricina* genes for 18S rRNA, ITS . . . | 333 | 9e−90 | 189/196 | (96%) |
| AF297667\|AF297667.1 *Umbilicaria muehlenbergii* isolate sm11004 1 . . . | 331 | 4e−89 | 182/187 | (97%) |
| AF297666\|AF297666.1 *Umbilicaria muehlenbergii* isolate sm11003 1 . . . | 331 | 4e−89 | 182/187 | (97%) |
| AF141190\|AF141190.1 *Neofabraea alba* 18S ribosomal RNA gene, par . . . | 331 | 4e−89 | 182/187 | (97%) |
| AF141189\|AF141189.1 *Neofabraea malicorticis* 18S ribosomal RNA g . . . | 331 | 4e−89 | 182/187 | (97%) |
| AF141181\|AF141181.1 *Pezicola ocellata* strain CBS267.39 18S ribo . . . | 331 | 4e−89 | 182/187 | (97%) |
| AF096204\|AF096204.1 *Umbilicaria muehlenbergii* 18S ribosomal RNA . . . | 331 | 4e−89 | 182/187 | (97%) |
| AF083199\|AF083199.1 *Phialophora* sp. p3901 18S ribosomal RNA, pa . . . | 331 | 4e−89 | 182/187 | (97%) |
| AF383949\|AF383949.1 *Botryosphaeria quercuum* 18S ribosomal RNA g . . . | 327 | 6e−88 | 190/197 | (96%), |

TABLE 11

| Sequences producing significant alignments: | | (bits) | Value | |
|---|---|---|---|---|
| AJ276062\|AJ276062.1 *Aureobasidium pullulans* 5.8S rRNA gene and . . . | 1043 | 0.0 | 526/526 | (100%) |
| AF182377\|AF182377.1 *Hormonema* sp. F-054, 764 internal transcribe . . . | 1011 | 0.0 | 510/510 | (100%) |
| AF121284\|AF121284.1 *Aureobasidium pullulans* strain ATCC42457 in . . . | 1007 | 0.0 | 508/508 | (100%) |
| AF013229\|AF013229.1 *Aureobasidium pullulans* 18S ribosomal RNA g . . . | 1005 | 0.0 | 556/567 | (98%), |
| AJ244269\|AJ244269.1 *Aureobasidium pullulans* 5.8S rRNA gene and . . . | 1003 | 0.0 | 506/506 | (100%) |
| AJ244236\|AJ244236.1 *Aureobasidium pullulans* 5.8S rRNA gene and . . . | 1003 | 0.0 | 506/506 | (100%) |
| AF121286\|AF121286.1 *Aureobasidium pullulans* var. melanigenum st . . . | 991 | 0.0 | 506/508 | (99%) |
| AF121285\|AF121285.1 *Aureobasidium pullulans* strain ATCC48433 in . . . | 959 | 0.0 | 502/508 | (98%) |
| AF121281\|AF121281.1 *Aureobasidium pullulans* strain ATCC11942 in . . . | 959 | 0.0 | 502/508 | (98%) |
| AJ244232\|AJ244232.1 *Aureobasidium pullulans* 5.8S rRNA gene and . . . | 955 | 0.0 | 500/506 | (98%) |
| AJ276061\|AJ276061.1 *Aureobasidium pullulans* 5.8S rRNA gene and . . . | 954 | 0.0 | 502/505 | (99%), |
| AJ244265\|AJ244265.1 *Trimmatostroma abietina* 5.8S rRNA gene and . . . | 942 | 0.0 | 500/507 | (98%), |
| AJ244233\|AJ244233.1 *Aureobasidium pullulans* 5.8S rRNA gene and . . . | 942 | 0.0 | 493/499 | (98%) |

TABLE 11-continued

| Sequences producing significant alignments: | (bits) | Value | |
|---|---|---|---|
| AJ244231\|AJ244231.1 *Aureobasidium pullulans* 5.8S rRNA gene and ... | 942 | 0.0 | 500/507 (98%), |
| AJ244235\|AJ244235.1 *Aureobasidium pullulans* 5.8S rRNA gene and ... | 932 | 0.0 | 497/506 (98%) |
| AJ244234\|AJ244234.1 *Aureobasidium pullulans* 5.8S rRNA gene and ... | 932 | 0.0 | 497/506 (98%) |
| AF121287\|AF121287.1 *Aureobasidium pullulans* var. melanigenum st ... | 924 | | 501/510 (98%), |

TABLES 12

| Sequences producing significant alignments: | (bits) | Value | |
|---|---|---|---|
| AJ276062\|AJ276062.1 *Aureobasidium pullulans* 5.8S rRNA gene and ... | 1021 | 0.0 | 525/527 (99%), |
| AF013229\|AF013229.1 *Aureobasidium pullulans* 18S ribosomal RNA g ... | 997 | 0.0 | 554/567 (97%), |
| AF182377\|AF182377.1 *Hormonema* sp. F-054,764 internal transcribe ... | 989 | 0.0 | 509/511 (99%), |
| AF121284\|AF121284.1 *Aureobasidium pullulans* strain ATCC42457 in ... | 985 | 0.0 | 507/509 (99%), |
| AJ244269\|AJ244269.1 *Aureobasidium pullulans* 5.8S rRNA gene and ... | 981 | 0.0 | 505/507 (99%), |
| AJ244236\|AJ244236.1 *Aureobasidium pullulans* 5.8S rRNA gene and ... | 981 | 0.0 | 505/507 (99%), |
| AF121286\|AF121286.1 *Aureobasidium pullulans* var. melanigenum st ... | 969 | 0.0 | 505/509 (99%), |
| AJ244265\|AJ244265.1 *Trimmatostroma abietina* 5.8S rRNA gene and ... | 965 | 0.0 | 502/507 (99%) |
| AJ244231\|AJ244231.1 *Aureobasidium pullulans* 5.8S rRNA gene and ... | 965 | 0.0 | 502/507 (99%) |
| AJ276061\|AJ276061.1 *Aureobasidium pullulans* 5.8S rRNA gene and ... | 940 | 0.0 | 502/506 (99%), |
| AF121287\|AF121287.1 *Aureobasidium pullulans* var. melanigenum st ... | 940 | 0.0 | 502/510 (98%), |
| AF121285\|AF121285.1 *Aureobasidium pullulans* strain ATCC48433 in ... | 938 | 0.0 | 501/509 (98%), |
| AF121281\|AF121281.1 *Aureobasidium pullulans* strain ATCC11942 in ... | 938 | 0.0 | 501/509 (98%), |
| AJ244232\|AJ244232.1 *Aureobasidium pullulans* 5.8S rRNA gene and ... | 934 | 0.0 | 499/507 (98%), |
| AY029406\|AY029406.1 *Astasia longa* internal transcribed spacer 1 ... | 932 | 0.0 | 531/546 (97%), |
| AJ244235\|AJ244235.1 *Aureobasidium pullulans* 5.8S rRNA gene and ... | 926 | 0.0 | 498/507 (98%), |
| AJ244234\|AJ244234.1 *Aureobasidium pullulans* 5.8S rRNA gene and ... | 926 | 0.0 | 498/507 (98%), |
| AJ244233\|AJ244233.1 *Aureobasidium pullulans* 5.8S rRNA gene and ... | 920 | 0.0 | 492/500 (98%), |
| AJ244252\|AJ244252.1 *Kabatiella lini* 5.8S rRNA gene and internal ... | 912 | 0.0 | 497/508 (97%), |
| AJ244251\|AJ244251.1 *Kabatiella caulivora* 5.8S rRNA gene and int ... | 872 | 0.0 | 492/508 (96%), |
| AF013225\|AF013225.1 *Phaeocryptopus gaeumannii* 18S ribosomal RNA ... | 454 | e-126 | 362/398 (90%), |
| AJ244257\|AJ244257.1 *Pringsheimia smilacis* 5.8S rRNA gene and in ... | 436 | e-121 | 256/264 (96%), |

EXAMPLE 50

Into a 30 ml volume test tube was put 5.5 ml of YM medium (Difco) and sterilized at 121° C. for 20 minutes. After cooling, the medium was inoculated with a platinum loopful of ADK-34 stored on a YPD-agar medium (Difco) slant and incubated at 26° C. for 4 days in a shake incubator to obtain a seed culture. Into another test tube was put 5.5 ml of Czapek's medium (Difco; sucrose concentration: 3 wt %), sterilized, and inoculated with 500 μl of the ADK-34 seed culture (5% inoculation), followed by cultivation at 26° C. for 4 days in a shake incubator (300 rpm). The culture was white and significantly viscous. After the cultivation, an equivalent amount of distilled water was added to the culture. The culture was autoclaved for 15 minutes and then centrifuged at 10,000 rpm for 15 minutes to obtain the culture solution (supernatant liquid) containing polysaccharides. The β-glucan content of the culture solution and its purity with respect to polysaccharide pullulan were measured in accordance with the methods described in Analysis Examples 1 and 3. As a result, the purity with respect to polysaccharide pullulan was 100%, and the β-glucan yield based on the sugar, calculated from the β-glucan content, was 44%. The culture solution had an absorbance of 0.030 at 490 nm, which indicates suppression of coloration. The β-glucan was found to have a molecular weight range of from 150,000 to 2,000,000 as measured in accordance with the method of Analysis Example 2. The culture solution was lyophilized to give sample L.

IFO-6353 was grown in the same manner as described above, and the β-glucan content of the culture solution and the purity with respect to polysaccharide pullulan were measured in the same manner as described above. The purity with respect to polysaccharide pullulan was 40%, and the yield of β-glucan based on the sugar was calculated to be 11%. The absorbance of the culture solution at 490 nm was 0.190, indicating pigmentation.

EXAMPLE 51

In 100 ml of distilled water was dissolved 1.7 g of Yeast Nitrogen Base w/o Amino Acids and Ammonium Sulfate (Difco), and the solution was sterilized by filtration. Separately, 5 g of sodium nitrate was dissolved in 500 ml of distilled water to prepare a sodium nitrate solution having a doubled concentration. Twelve weight percent carbon source aqueous solutions were prepared using each of sucrose, glucose, fructose, soluble starch, and maltose (Wako Pure Chemical). The sodium nitrate solution, aqueous carbon source solutions, and distilled water were each autoclaved at 121° C. for 20 minutes. Into a sterile test tube were put 1 ml of the Yeast Nitrogen Base w/o Amino Acids and Ammonium Sulfate, 5 ml of the sodium nitrate solution, 2.5 ml of each of the carbon source aqueous solutions, and 1.5 ml of distilled water to make 10 ml to prepare media for examining carbon source utilization (checking media).

Into a 30 ml volume test tube was put 5.5 ml of YM medium (Difco) and sterilized at 121° C. for 20 minutes. After cooling, the medium was inoculated with a platinum loopful of ADK-34 stored on a YPD-agar medium (Difco) slant and incubated at 26° C. for 4 days in a shake incubator to obtain a seed culture. The ADK-34 seed culture was inoculated into each of the above-prepared checking media, followed by cultivation at 26° C. for 5 days in a shake incubator (300 rpm). All the cultures were white and significantly viscous. After the cultivation, an equivalent amount of distilled water was added to each of the cultures. The culture was autoclaved for 15 minutes and then centrifuged at 10,000 rpm for 15 minutes to obtain the culture solution (supernatant liquid) containing polysaccharides. The β-glucan content of the culture solution and its purity with respect to polysaccharide pullulan were measured in accordance with the methods described in Analysis Examples 1 and 3. The results of measurements are shown in Table 13 below. As is apparent from Table 13, the purity with respect to polysaccharide pullulan was 90% or higher, and the β-glucan yield based on the sugar was calculated to range from 20 to 46% with any of the carbon sources. The culture solution had an absorbance of 0.026 to 0.041 at 490 nm, which indicates suppression of coloration. The β-glucan was found to have a molecular weight range of from 150,000 to 2,000,000 as measured in accordance with the method of Analysis Example 2.

TABLE 13

| Carbon Source | Purity (%) | β-Glucan Yield based on Sugar (%) | Absorbance of Culture Solution (490 nm) |
|---|---|---|---|
| Sucrose | 100 | 46 | 0.031 |
| Glucose | 110 | 44 | 0.033 |
| Fructose | 104 | 20 | 0.031 |
| Soluble starch | 96 | 34 | 0.041 |
| Maltose | 94 | 29 | 0.026 |

EXAMPLE 52

ADK-34 was inoculated into YM medium and incubated at 26° C. for 3 days to obtain 300 ml of a seed culture. Into a 5 liter volume jar fermentor equipped with impellers "FULLZONE" (B.E. Marubishi Co., Ltd.) were put 3 liters of Czapek's medium and 300 g of sucrose. After sterilization and cooling, the medium was inoculated with 100 ml of the seed culture, followed by cultivation at 26° C. for 72 hours to obtain a culture measuring 3 liters. The culture (3 liters) was sterilized by heating at 80° C. for 30 minutes, mixed with an equivalent amount of distilled water, followed by mixing well. The mixture was centrifuged at 8000 rpm, for 15 minutes to get diluted culture. The resulting diluted culture was further diluted 5-fold with distilled water. The absorbance of the diluted culture at 490 nm was 0.023. To 100 ml of the diluted culture was added an equivalent amount of ethanol. The thus formed precipitate was collected, washed with ethanol, and dissolved in 50 ml of distilled water. The ethanol precipitation was repeated once more, and the resulting aqueous solution was put into a dialysis bag (molecular weight cut: 3000) and dialyzed against 10 times the volume of distilled water to finally obtain 100 ml of a polysaccharide solution. The β-glucan content was 25 mg/ml; the purity with respect to polysaccharide pullulan was 95%; and the molecular weight of the β-glucan ranged 150,000 to 2,000,000.

EXAMPLE 53

Beta-Glucan-Containing Fat and Oil Composition

A hundred parts of sample L and 100 parts of soybean oil were thoroughly mixed in a kneader. The mixture was allowed to stand at 60° C. for 10 minutes and then cooled to room temperature to obtain a creamy β-glucan-containing fat and oil composition of the invention. The composition was found to have β-glucan uniformly dispersed therein.

INDUSTRIAL APPLICABILITY

The β-glucan-containing fat and oil composition of the present invention has β-glucan exhibiting excellent bioregulatory functions uniformly dispersed therein. Added to a food, etc., the composition provides the food with uniformly dispersed β-glucan and also with enhanced taste, texture, stability, and the like. Use of the microorganisms according to the present invention makes it possible to produce high-activity and high-quality β-glucan from inexpensive sugars such as sucrose with good efficiency at high production rates.

The invention claimed is:

1. A biologically pure strain of *Aureobasidium pullulans* isolated from a food source, the strain having a gene selected from an 18S rRNA gene containing SEQ ID No.1 and an ITS-5.8S rRNA gene containing SEQ ID No. 2, wherein the strain is capable of producing and secreting β-glucan, and wherein the strain is *Aureobasidium pullulans* ADK-34 (FERM BP-8391).

2. The isolated strain of *Aureobasidium pullalans* according to claim 1, wherein the strain has resistance to the antibiotic cycloheximide.

3. A process of producing β-glucan, the process comprising culturing an isolated strain of *Aureobasidium pullulans* ADK-34 (FERM BP-8391) according to claim 1, wherein said strain produces and secretes β-glucan from said culturing.

4. The process according to claim 3, wherein the culturing of the *Aureobasidium pullulans* comprises culturing in a medium containing saccharides as a carbon source.

* * * * *